United States Patent
Eastman

(10) Patent No.: US 10,952,645 B2
(45) Date of Patent: Mar. 23, 2021

(54) METHOD AND APPARATUS FOR DETERMINING A TYPE OF DATA AND AN INTEGRITY OF DATA

(71) Applicant: Under Armour, Inc., Baltimore, MD (US)

(72) Inventor: Kyler Eastman, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 390 days.

(21) Appl. No.: 15/252,536

(22) Filed: Aug. 31, 2016

(65) Prior Publication Data

US 2018/0056126 A1 Mar. 1, 2018

(51) Int. Cl.
| | | |
|---|---|---|
| *A61B 5/11* | (2006.01) | |
| *G06K 9/00* | (2006.01) | |
| *A61B 5/0205* | (2006.01) | |
| *A61B 5/024* | (2006.01) | |
| *H04L 29/08* | (2006.01) | |
| *A61B 5/00* | (2006.01) | |

(52) U.S. Cl.
CPC .......... *A61B 5/1118* (2013.01); *G06K 9/0055* (2013.01); *G06K 9/00342* (2013.01); *A61B 5/024* (2013.01); *A61B 5/0205* (2013.01); *A61B 5/681* (2013.01); *A61B 5/6801* (2013.01); *A61B 5/6805* (2013.01); *H04L 67/22* (2013.01)

(58) Field of Classification Search
None
See application file for complete search history.

(56) References Cited

U.S. PATENT DOCUMENTS

| | | | | |
|---|---|---|---|---|
| 2002/0091329 A1* | 7/2002 | Heikkila | .............. | A61B 5/0255 600/500 |
| 2006/0155218 A1* | 7/2006 | Heinks | .................. | A61B 5/1118 600/595 |
| 2006/0255955 A1* | 11/2006 | O'Connor | ............ | A61B 5/6828 340/573.1 |
| 2009/0150178 A1* | 6/2009 | Sutton | ................... | A61B 5/1112 705/2 |
| 2011/0087137 A1* | 4/2011 | Hanoun | ............... | A61B 5/0205 600/587 |
| 2013/0190903 A1* | 7/2013 | Balakrishnan | ....... | A61B 5/7246 700/91 |
| 2013/0274587 A1* | 10/2013 | Coza | .................... | A61B 5/6804 600/409 |
| 2013/0274904 A1* | 10/2013 | Coza | ....................... | G06F 3/011 700/91 |
| 2014/0031959 A1* | 1/2014 | Glode | ................. | G06F 19/3481 700/91 |
| 2014/0156228 A1* | 6/2014 | Molettiere | ............. | G16H 10/60 702/189 |
| 2014/0164611 A1* | 6/2014 | Molettiere | ............ | A61B 5/1112 709/224 |
| 2014/0228649 A1* | 8/2014 | Rayner | ................. | A61B 5/1118 600/301 |

(Continued)

*Primary Examiner* — Lina M Cordero
(74) *Attorney, Agent, or Firm* — Maginot, Moore & Beck LLP

(57) ABSTRACT

A method of operating an activity tracking system includes collecting activity data from an activity tracking device, receiving an activity type associated with the activity data via a user input, and evaluating the collected activity data to determine whether one or more aspects thereof are within a predetermined range of values assigned to the received activity type.

21 Claims, 11 Drawing Sheets

(56) References Cited

U.S. PATENT DOCUMENTS

| | | | |
|---|---|---|---|
| 2014/0278220 A1* | 9/2014 | Yuen | G01B 21/16 702/150 |
| 2016/0106360 A1* | 4/2016 | Choi | A61B 5/0205 434/247 |
| 2017/0039480 A1* | 2/2017 | Bitran | G16H 50/20 |
| 2017/0155978 A1* | 6/2017 | Noh | A61B 5/6807 |

* cited by examiner

RUN / WALK                                          296

| AVERAGE SPEED (MPH) | 0 - 2 | 2 - 4 | 4 - 6 | 6 + |
|---|---|---|---|---|
| HEART RATE (BPM) | 100 | 135 | 160 | 170 |
| TOLERANCE RANGE (10%) | 90 - 110 | 122 - 149 | 144 - 176 | 153 - 187 |

FIG. 8A

CYCLING                                             298

| AVERAGE SPEED (MPH) | 0 - 5 | 5 - 10 | 10 - 15 | 15 + |
|---|---|---|---|---|
| HEART RATE (BPM) | 100 | 130 | 140 | 150 |
| TOLERANCE RANGE (10%) | 81 - 99 | 117 - 143 | 126 - 154 | 135 - 165 |

FIG. 8B

RUN / WALK 314

| | | | | |
|---|---|---|---|---|
| SPEED (MPH) | 0 - 2 | 2 - 4 | 4 - 6 | 6 + |
| HEART RATE (BPM) | 100 | 130 | 160 | 170 |
| RESPIRATION RATE (BPM) | 12 | 20 | 25 | 35 |
| STEP RATE (SPM) | 100 | 130 | 160 | 180 |
| TEMPERATURE (F) | 99.0 | 100.0 | 101.0 | 102.0 |

FIG. 10A

CYCLING 316

| | | | | | |
|---|---|---|---|---|---|
| SPEED (MPH) | 0 - 5 | 5 - 10 | 10 - 15 | 15 - 20 | 20 + |
| HEART RATE (BPM) | 90 | 110 | 140 | 150 | 160 |
| RESPIRATION RATE (BPM) | 12 | 15 | 20 | 25 | 35 |
| TEMPERATURE (F) | 99.0 | 99.5 | 100.0 | 100.5 | 100.9 |

FIG. 10B

SWIMMING 318

| | | | | | |
|---|---|---|---|---|---|
| SPEED (MPH) | 0 - 1 | 1 - 2 | 2 - 3 | 3 - 4 | 4 + |
| HEART RATE (BPM) | 100 | 145 | 160 | 170 | 175 |
| RESPIRATION RATE (BPM) | 8 | 12 | 15 | 18 | 20 |

FIG. 10C

METHOD AND APPARATUS FOR DETERMINING A TYPE OF DATA AND AN INTEGRITY OF DATA

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This disclosure relates to the field of activity monitoring systems and in particular to processing activity data generated by an activity monitoring system to determine a type and integrity thereof.

BACKGROUND

Active individuals, such as walkers, runners, and other athletes commonly use activity tracking devices to track fitness data and route data. For example, runners, cyclists, and swimmers may utilize an activity tracking device to determine the distance and duration of a workout.

One approach for determining the distance traversed by a user during a workout and the speed of the user during the workout is to track the user using the global positioning system ("GPS"). By recording the time and location of the user during the workout, the activity tracking device is able to calculate useful analytics, such as the total distance traversed by the user, the average speed of the user, and the maximum speed of the user, for example.

In order to provide accurate analytics to the user, the activity tracking device should record workout data only when the user is performing a workout. For example, consider a user who completes a workout and then takes a bus back to her home. The activity tracking device should record fitness data and route data only for the duration of the workout, and not when the user is riding the bus. If the activity tracking device records fitness data and route data while the user is riding the bus, then the recorded data typically becomes corrupt and the analytics provided by the activity tracking device do not reflect the workout performed by the user. Present activity tracking devices cannot automatically determine when the user has ended the workout and started riding the bus, thereby increasing the likelihood of the user accidentally corrupting the recorded activity data.

Moreover some users, such as triathletes, change activities mid-workout. For example, a user may start a workout swimming, switch to cycling, and then conclude with a run. The typical activity tracking device cannot automatically determine when the user has changed from swimming to cycling and from cycling to running. Accordingly, the user is required to update settings on the activity tracking device during her workout. Such a process is typically viewed as a significant inconvenience to most users, because attention is diverted from the workout to the activity tracking device.

Accordingly, improvements in activity tracking devices and in the processing of the fitness data generated by activity tracking devices are desirable in order to increase the usefulness and integrity of the fitness data.

SUMMARY

According to an exemplary embodiment of the disclosure, a method of operating an activity tracking system includes collecting activity data from an activity tracking device, receiving an activity type associated with the activity data via a user input, and evaluating the collected activity data to determine whether one or more aspects thereof are within a predetermined range of values assigned to the received activity type.

According to another exemplary embodiment of the disclosure, a non-transient computer readable medium containing computer executable instructions which are configured to, when executed by a processor: receive activity data from an activity tracking device; compare the activity data to known values and patterns for a first activity type; based on the comparison, determine whether the activity data is verified; when the data is verified, assign the first activity type to the activity data and update a user profile; when the activity data is not verified, determine whether the activity data may be compared to a second activity type.

According to yet another exemplary embodiment of the disclosure, an activity tracking system includes at least one sensor configured to generate activity data, a user input configured to receive an activity type associated with the generated activity data, and an interface configured (i) to collect the generated activity data, and (ii) to evaluate the generated activity data to determine whether one or more aspects thereof are within a predetermined range of values assigned to the received activity type.

BRIEF DESCRIPTION OF THE FIGURES

The above-described features and advantages, as well as others, should become more readily apparent to those of ordinary skill in the art by reference to the following detailed description and the accompanying figures in which:

FIG. 8A is a chart illustrating an exemplary individualized data set including data related to a user's physiological characteristics while running;

FIG. 8B is a chart illustrating an exemplary individualized data set including data related to a user's physiological characteristics while cycling;

FIG. 10A is a chart illustrating an exemplary individualized data set including data related a user's physiological characteristics while running;

FIG. 10B is a chart illustrating an exemplary individualized data set including data related a user's physiological characteristics while cycling; and FIG. 10C is a chart illustrating an exemplary individualized data set including data related a user's physiological characteristics while swimming.

All Figures© Under Armour, Inc. 2016. All rights reserved.

DETAILED DESCRIPTION

Disclosed embodiments include systems, apparatus, methods and storage medium associated with processing data generated by an activity tracking system.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
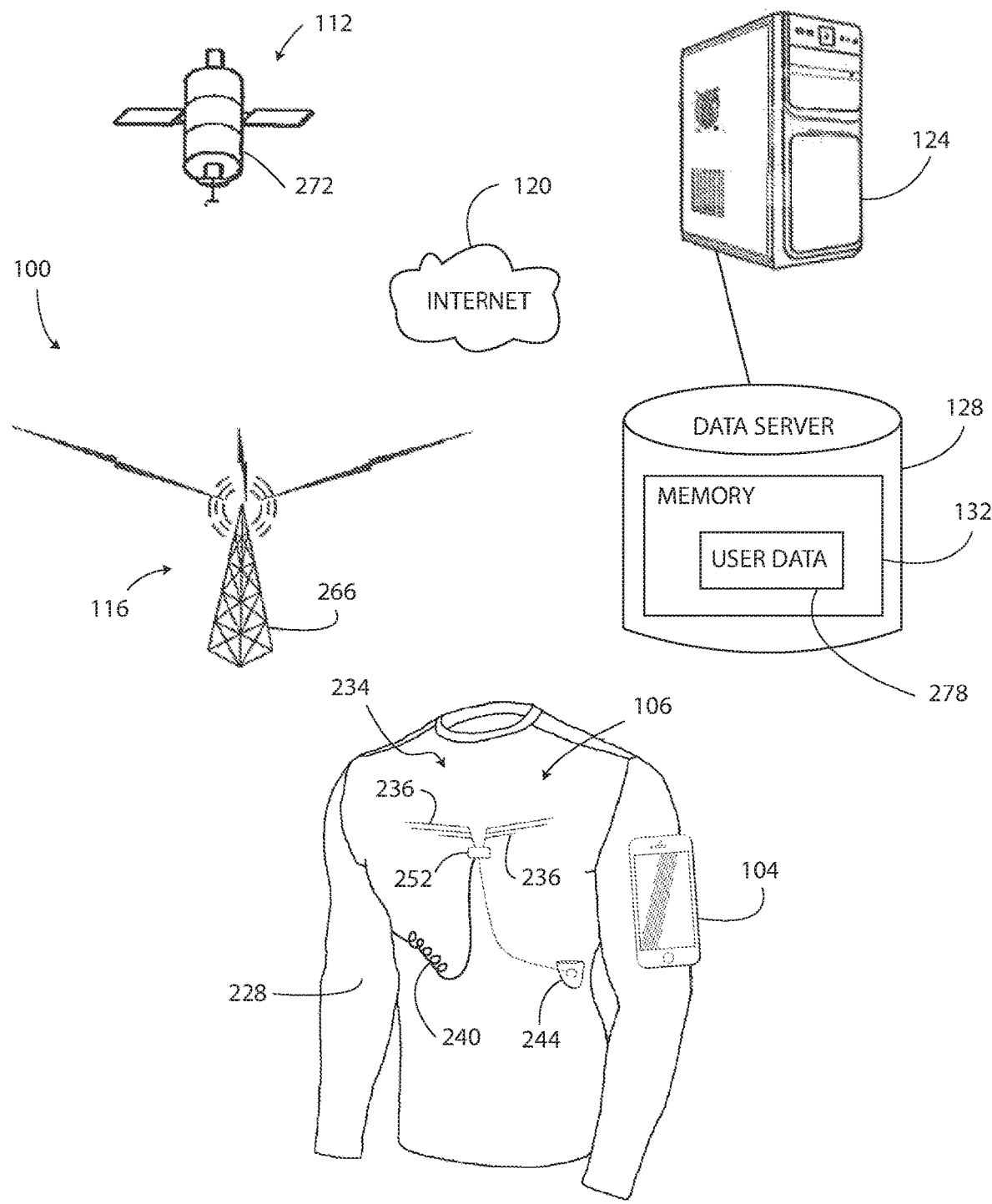
FIG. 1 is a block diagram of an activity tracking system, as disclosed herein.

As shown in FIG. 1, an exemplary embodiment of an activity tracking system 100 includes a personal electronic device 104, a sensor assembly 106, a GPS satellite 112, a cellular network 116, a wide area network such as the Internet 120, a remote computer 124, and a data server 128 including a memory unit 132. At least one of the personal electronic device 104 and the sensor assembly 106 provides an activity tracking device that is configured to generate activity data associated with an activity type performed by the user. In at least one embodiment, the activity data is associated with an activity type that is selected by the user (e.g., running, walking, bicycling, etc.). The activity tracking system 100 processes the activity data to determine whether the activity data was generated as a result of the associated activity type. If the activity data is consistent with the associated activity type, the activity tracking system 100 verifies the activity data and the activity data is stored in the data server 128. However, if the activity data is not consistent with the associated activity type, the activity tracking system 100 does not verify the activity data. Unverified activity data is typically discarded or saved separately from the verified activity data, and is not associated with the electronic data profile of the user. In this way, the activity tracking system 100 ensures that the activity data associated with a user's electronic data profile is associated with activity types that were actually performed by the user.

In the illustrated embodiment of FIG. 1, one or both of the personal electronic device 104 and the sensor device 106 may serve as activity tracking devices. The personal electronic device 104 is shown in FIG. 1 as a smartphone; however, other apparatus including a tablet computer, a smart watch, or other wearable and/or portable electronic devices may be utilized. In various embodiments, the personal electronic device 104 may be configured for placement in a shoe (not shown) or attached to the shoe, may be carried in a pocket (not shown) of the user's clothing, and/or may be attached to any portion of the user or the user's clothing. In yet another embodiment, the personal electronic device 104 includes or is connectable to a strap (not shown) to mount the device 104 onto the user. In this embodiment, the personal electronic device 104 may be strapped to the user's arm, wrist, ankle, or worn around the chest of the user. For example, the personal electronic device 104 is provided as a watch or a watch-like electronic device. In an alternative embodiment, the personal electronic device 104 is mounted (permanently or removably) on the user or the user's clothing, footwear or other article of apparel using any of various mounting means such as adhesives, stitching, pockets, or any of various other mounting means. Accordingly, at least the personal electronic device 104 is configured to be located proximate to the user during activities such as hiking, running, jogging, walking, swimming, cycling, and/or the like.

Figure 2:
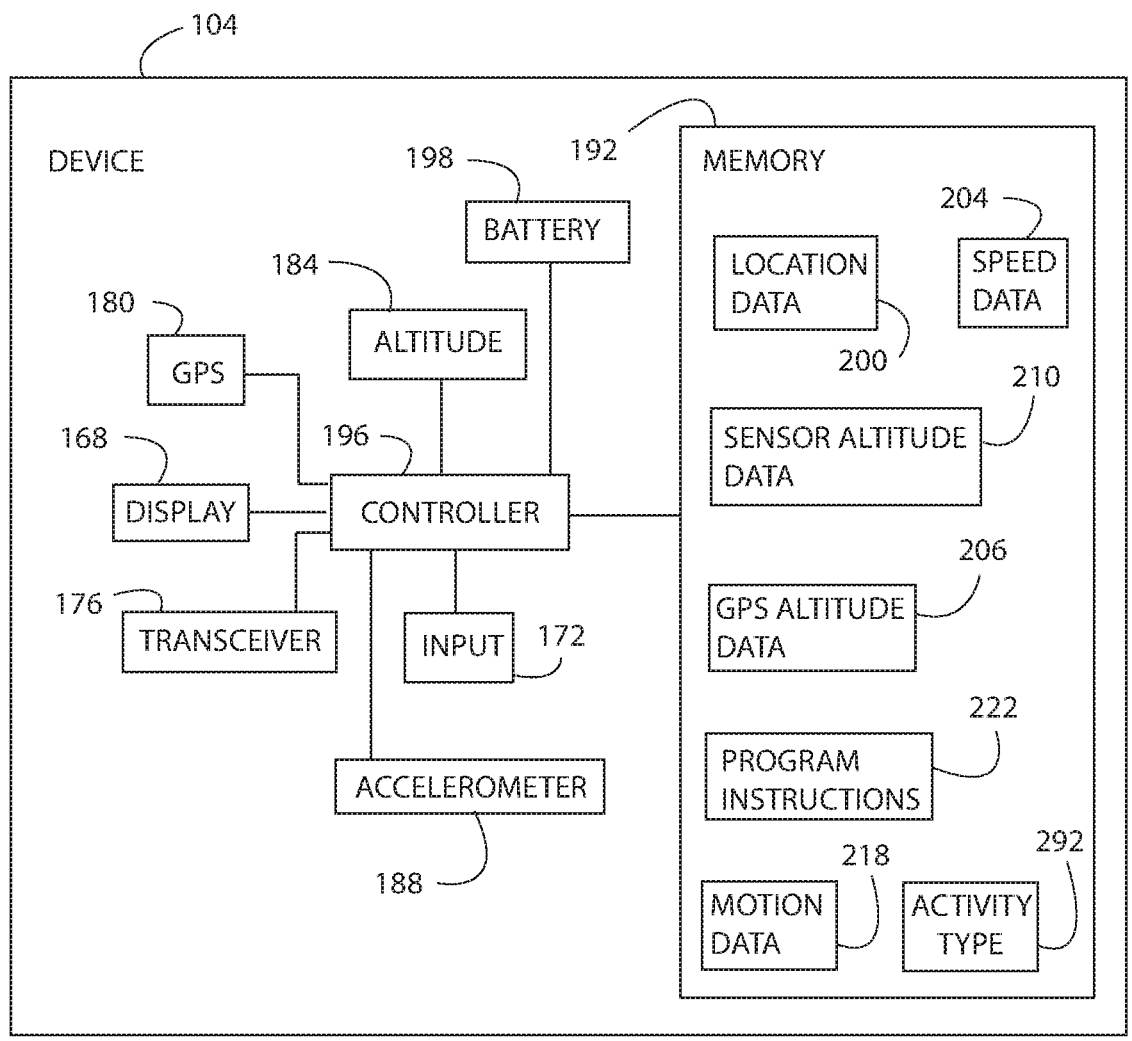
FIG. 2 is a block diagram of the personal electronic device of the activity tracking system shown in FIG. 1.

With reference to FIG. 2, an exemplary personal electronic device 104 is shown. The personal electronic device 104 includes a display unit 168, an input unit 172, a transceiver 176, a GPS receiver 180, an altimeter 184, an accelerometer 188, a memory 192, and a battery 198, each of which is operably connected to a controller or processor 196. It is appreciated that additional components (not shown) may further be provided to facilitate functioning of the device. In addition, one or more of the listed components may be omitted and/or provided in additional devices in communication with those listed herein.

The display unit 168 may comprise a liquid crystal display (LCD) panel configured to display text, images, and other visually comprehensible data. The display unit 168, in another embodiment, is any display unit as desired by those of ordinary skill in the art, including, but not limited to, an active-matrix organic light-emitting diode display. The display unit 168 is configurable to display, for example, one or more interactive interfaces or display screens, including a display of a distance traversed by the user, the activity type performed by the user, and physiological characteristics of the user during a workout.

The input unit 172 is configured to receive data input via manipulation by a user. The input unit 172 may be configured as a touchscreen applied over the display unit 168 that is configured to enable a user to input data via the touch of a finger and/or a stylus. In another embodiment, the input unit 172 comprises any device configured to receive input data, as may be utilized by those of ordinary skill in the art, including, for example, one or more buttons, switches, keys, microphones, and/or the like. The input unit 172 is also referred to herein as a user input.

In FIG. 2, the transceiver 176, which may also be referred to as a wireless transmitter and/or receiver, is configured to wirelessly transmit data to the sensor assembly 106 and to wirelessly receive data from the sensor assembly 106 either directly or indirectly via a direct wireless electrical communication link, a cellular network 116 (FIG. 1), a wireless local area network ("Wi-Fi"), a personal area network, a wide area network, the Internet 120, and/or any other wireless network. The transceiver 176 is may also communicate with other network devices, such as e.g., the remote server 124. The transceiver 176 is compatible with any desired wireless communication standard or protocol including, but not limited to, Near Field Communication ("NFC"), IEEE 802.11, IEEE 802.15.1 ("Bluetooth®"), Global System for Mobiles ("GSM"), and Code Division Multiple Access ("CDMA").

The GPS (Global Positioning System) receiver 180 is configured to receive GPS signals from the GPS satellite 112 (see FIG. 1). The GPS receiver 180 is further configured to receive altitude data 206. A processor in communication with the GPS receiver 180 may be configured to generate location/distance data 200, speed data 204, etc. based on the received GPS signals (e.g., processor 196). Alternatively, a separate speed sensor may be utilized to generate the speed data 204. The location/distance data 200 is representative of a location on the Earth of the personal electronic device 104 based on the received GPS signals. The location data 192, in one embodiment, includes latitude and longitude information and is used by the controller 196 to determine a precise location and/or a distanced traversed by the user. In alternative embodiments, the location/distance data 200 is provided in any other form, such as Geographic Information System ("GIS") data or as data input by the user with the input unit 172. In another alternative, a separate location sensor is provided, which may be utilized to process the latitude and longitude data into a precise location and/or distance travelled. The speed data 204 is representative of the speed of the personal electronic device 104 as it moves upon the Earth. The altitude data 206 is representative of the altitude of the personal electronic device 104. In one embodiment, the GPS receiver 180 is referred to as an altitude sensor. The controller 196 is configured to store the location/distance data 200, the speed data 204, and the GPG altitude data 206 generated by the GPS receiver 180 in the memory 192. In another embodiment, the GPS receiver 180 is not used to generate the altitude data 206 and only the altimeter 184 is used to determine the altitude of the personal electronic device 104.

The altimeter 184 of the personal electronic device 104 is a sensor configured to generate sensor altitude data 210 that is representative of the altitude of the personal electronic device 104. In one embodiment, the altimeter 184 is a barometric pressure sensor that is configured to generate the sensor altitude data 210 based on sensed changes in barometric pressure. In another embodiment, the altimeter 184 is provided as another sensor type that is typically used to sense altitude. In yet another embodiment, the personal electronic device 104 does not include the altimeter 184 and the GPS receiver 180 or other device is used to determine the altitude of the personal electronic device 104.

The accelerometer 188 is a sensor configured to generate motion data 218 while being carried, worn, and/or utilized by the user. When the user is walking, running, hiking, jogging, or otherwise engaged in a bipedal motion activity, the motion data 218 may comprise a number of rhythmic peaks 302 (e.g., see FIG. 9, discussed in detail below) the frequency of which corresponds to a step rate (i.e., the speed at which the user takes steps while moving, such as sixty steps per minute) of the user. Accordingly, in some embodiments, the motion data 218, and, in particular, the step rate, is used by the personal electronic device 104 to determine a distance traversed by the user and the activity being performed by the user, as discussed elsewhere herein. When the user is engaged in a non-bipedal motion activity, such as swimming, cycling, kayaking, canoeing, and the like, the motion data 218 corresponds to the activity being performed by the user, as discussed elsewhere herein and as plotted in FIG. 9. The accelerometer 188 is provided as any type of accelerometer, such as a single-axis or a multi-axis microelectromechanical (MEMS) accelerometer. In other embodiments, the accelerometer 188 is provided as any type of accelerometer or other device configured to generate the motion data 218

The memory 192, as shown in FIG. 2, is an electronic data storage unit, which is also referred to herein as a non-transient computer readable medium. In one embodiment memory 192 is configured to store the location/distance data 200, the speed data 204, the altitude data 206, the sensor altitude data 210, the motion data 218, program instruction data 222, and activity type data 292, as well as any other electronic data associated with operating the personal electronic device 104 and the sensor assembly 106. In another alternative, the data is stored at a data storage entity remote to the personal electronic device 104 yet in communication therewith (such as via the network). The program instruction data 222 includes computer executable instructions for determining an activity type being performed by the user and/or for verifying the integrity of the data generated by the personal electronic device 104, as explained in further detail below. The activity type data 292 includes data corresponding to a type of activity being performed by a user of the activity tracking system 100, such as running, walking, jogging, cycling, swimming, and the like (e.g., see the exemplary activity type data of FIG. 7).

The controller or processor 196 is configured to execute the program instruction data 222 in order to control the display unit 168, the input unit 172, transceiver 176, the GPS receiver 180, the altimeter 184, the accelerometer 188, the memory 192, and the sensor assembly 106. The controller 196 is a provided as a microprocessor, a processor, or any other type of electronic control chip. The controller 196 may execute one or more software applications configured to derive information from the raw data collected at the device, including e.g., speed, location, distance, etc.

The battery 198 is electrically connected to at least the controller 196 and is configured supply electrical energy to each component of the personal electronic device 104 including the display unit 168, the input unit 172, the transceiver 176, the GPS receiver 180, the altimeter 184, the accelerometer 188, the memory 192, and the controller 196. The battery 198, in one embodiment is provided as a rechargeable lithium-ion battery cell(s). In other embodiments, the battery 198 is provided as any other suitable electrical power source.

Figure 3:
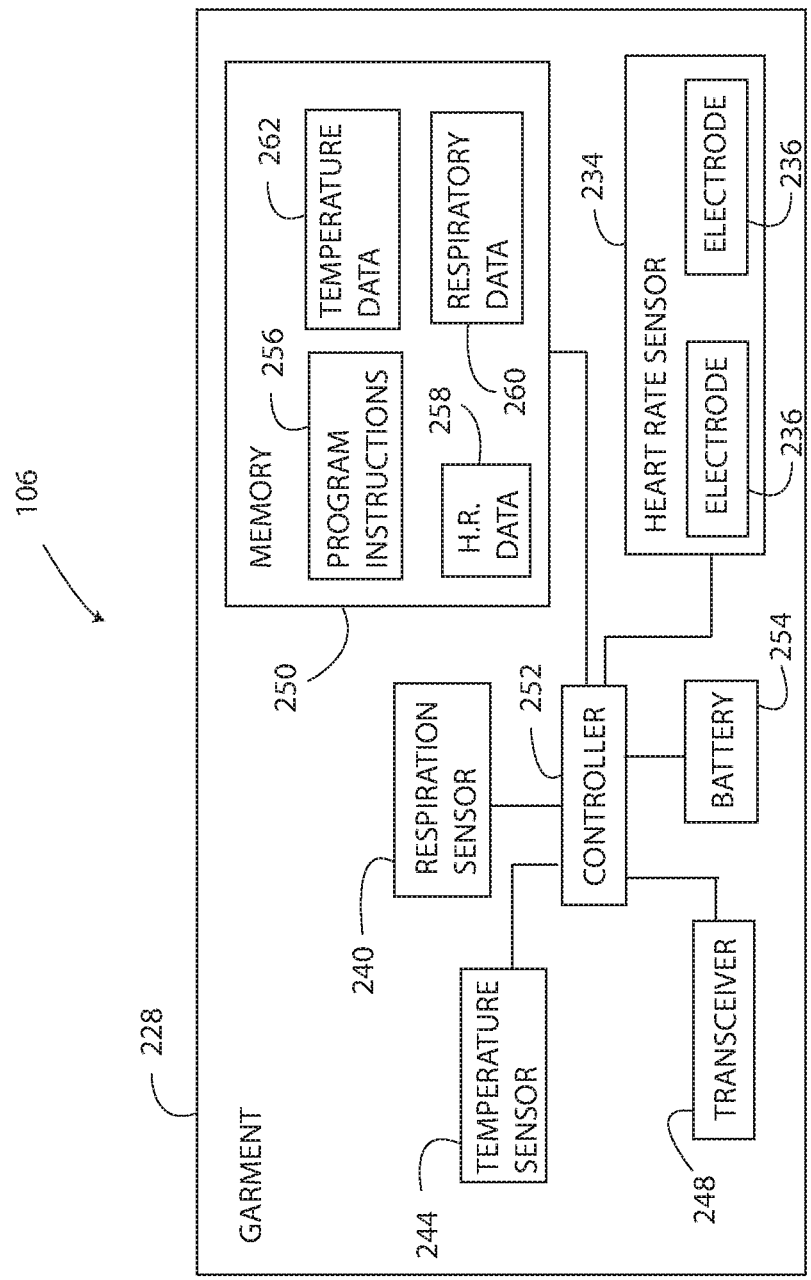
FIG. 3 is a block diagram of the sensor assembly of the activity tracking system shown in FIG. 1.

With reference now to FIGS. 1 and 3, an exemplary sensor assembly 106 is shown including at least one sensor coupled to a wearable item. The at least one sensor may be provided in any of various forms such as one or more of a heart rate sensor, an accelerometer, a respiratory sensor, a temperature sensor, a GPS receiver, or any of various other types of sensors. The wearable item may be provided in any of various forms such as a garment, a chest band, a wrist band, an article of footwear, an accessory, or any of various other wearable items. In the exemplary embodiment of FIGS. 1 and 3, the sensor assembly includes a garment 228, a heart rate sensor 234, a respiratory sensor 240, a temperature sensor 244, a transceiver 248, a memory 250, and a battery 254 each of which is electrically connected to a controller 252. It is appreciated that other and/or additional sensors may be provided as well. The garment 228 (also shown in FIG. 1), in the illustrated embodiment, is provided as an athletic shirt that is configured to properly position the heart rate sensor 234, the respiratory sensor 240, and the temperature sensor 244 on the user's body. In other embodiments, the heart rate sensor 234, the respiratory sensor 240, and the temperature sensor 244 are mounted to a strap (not shown) instead of, or in addition to, the garment 228. The strap is worn around the user's chest, arm, or leg, for example.

The heart rate sensor 234, in one embodiment, includes two electrodes 236, which are mechanically connected to the garment 228 and are configured to generate electrical data that is representative of the heart rate of the user. Another number and/or arrangement or array may be used with equal success. The heart rate data 258 generated by the heart rate sensor 234 is stored at least in the memory 250 of the sensor assembly 106. Exemplary heart rate data 258 is plotted in FIG. 7 and is described in detail further herein. At least a portion of each electrode 236 is formed from an electrically conductive material to enable the electrodes 236 to sense the electrical signals associated with the user's heart rate. The electrodes 236 are configured to be placed in direct contact with the skin of the user. The electrodes 236 are provided as any suitable type of electrode for detecting the heart rate of a user. Alternative methods for obtaining heart rate may be used in addition or in the alternative.

With continued reference to FIGS. 1 and 3, the respiratory sensor 240 is mechanically connected to the garment 228 and is configured to generate respiratory data 260 that is representative of a breathing rate of the user. The respiratory data 260 generated by the respiratory sensor 240 is stored in the memory 250 of the sensor assembly 106. Exemplary respiratory data 260 generated by the respiratory sensor 240 is plotted in FIG. 9 and is described in detail further below. Typically, the respiratory sensor 240 is configured to flex, stretch, or otherwise move in response to the motion of the user's chest while breathing. The respiratory sensor 240 converts the movement of the user into the respiratory data 260, which corresponds to the user's breathing rate. In another embodiment, the respiratory sensor 240 is provided as any suitable type of respiratory sensor.

Figure 9:
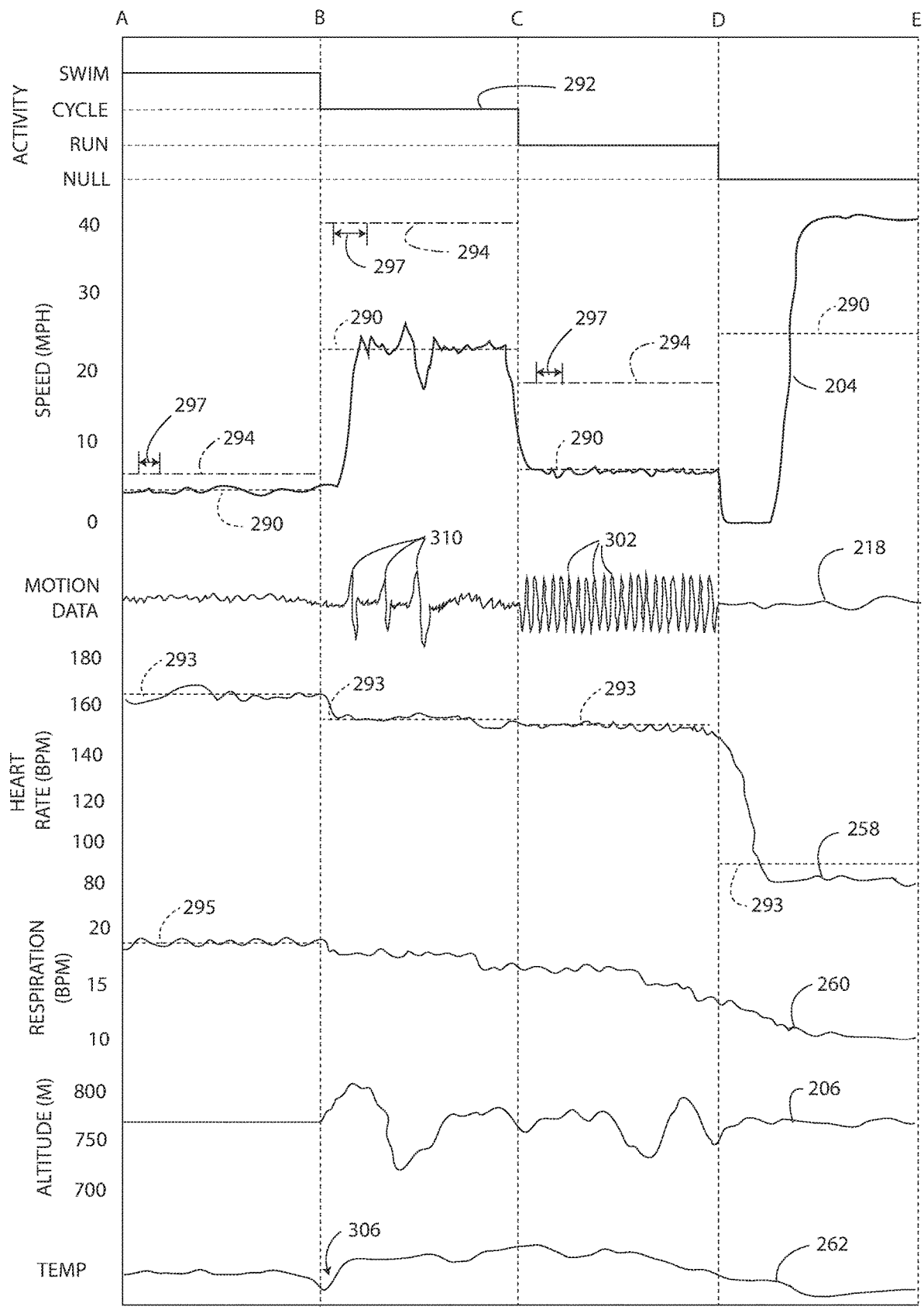
FIG. 9 is plot of exemplary activity type data, speed data, motion data, heart rate data, respiration rate data, altitude data, and temperature data verses time, the data generated by the activity tracking device of FIG. 1.

The temperature sensor 244 is mechanically connected to the garment 228 in one embodiment, and is configured to generate temperature data 262, as shown in FIG. 9, which is representative of the body temperature of the user. The temperature data 262 is stored in the memory 250 of the sensor assembly 106. The temperature sensor 244 is configured for placement against the skin of the user or at least in close proximity to the skin of the user so that the body temperature of the user is detectable by the temperature sensor 244. Alternatively, the temperature sensor 244 may be provided as any suitable type of temperature sensor.

As shown in FIG. 3 another exemplary device is provided. As shown the device comprises a garment 228, which comprises a transceiver 248, which is also referred to as a wireless transmitter and/or receiver, is configured to wirelessly communicate with the transceiver 176 of the personal electronic device 108 either directly or indirectly via the cellular network 116, a wireless local area network ("Wi-Fi"), a personal area network, and/or any other wireless network. The transceiver 248 is configured to transmit the heart rate data 258, the respiratory data 260, and the temperature data 262, among other data, to the transceiver 176 of the personal electronic device 104. Accordingly, the transceivers 176, 248 are compatible with any desired wireless communication standard or protocol including, but not limited to, Near Field Communication ("NFC"), IEEE 802.11, IEEE 802.15.1 ("Bluetooth®"), Global System for Mobiles ("GSM"), and Code Division Multiple Access ("CDMA").

The memory 250 is an electronic data storage unit, which is also referred to herein as a non-transient computer readable medium. The memory 250 is configured to store program instruction data 256 for operating the sensor assembly 106, as well as any other electronic data associated with operating the sensor assembly 106, such as the heart rate data 258, the respiratory data 260, and the temperature data 262. Alternatively, the herein described data may be stored at a separate entity in communication with the device yet remote therefrom.

The controller or processor 252 is configured to execute the program instruction data 256 in order to control the electrodes 236, the respiratory sensor 240, the temperature sensor 244, the transceiver 248, and the memory 250. The controller 252 is a provided as a microprocessor, a processor, or any other type of electronic control chip. In particular, the controller 252 may be configured to execute one or more software applications which processes collected raw data to derive information therefrom.

The battery 254 is electrically connected to at least the controller 252 and is configured supply electrical energy to each component of the sensor assembly 106 including the respiratory sensor 240, the temperature sensor 244, the transceiver 248, the memory 250, and the controller 252. The battery 254, in one embodiment is provided as a rechargeable lithium-ion battery cell(s). In other embodiments, the battery 254 is provided as any other suitable electrical power source.

Referring again to FIG. 1 both the sensor assembly 106 and the personal electronic device 104 have been shown as activity tracking devices that may be associated with a single user. However it will be recognized that a user may be associated with only a single activity tracking device (e.g., either a personal electronic device 104 or a sensor assembly 106) in one embodiment. In the embodiment of FIG. 1, the activity tracking device is configured to communicate with the remote computer 124 via a network of electrically interconnected computers and other electrical devices, such as the Internet 120. The Internet 120 enables electrical communication between each of the devices electrically connected thereto using any of various wired or wireless communications means.

As shown in FIG. 1, the cellular network 116 includes a plurality of cellular towers 266 (only one of which is illustrated). The transceiver 176 of the personal electronic device is configured to wirelessly communicate with the cell towers 266 to operatively connect the personal electronic device to the Internet 120.

The activity tracking system 100 is configured to receive signals from the GPS 112. The GPS 112 includes a plurality of satellites 272 (only one of which is illustrated in FIG. 1) that orbit the Earth and emit a geolocation signal. Upon receiving a suitable number of geolocation signals, GPS capable devices, such as the personal electronic device 104 (and in some embodiments the sensor assembly 106), are able to determine the current position of the device on the Earth. Moreover, the GPS capable devices disclosed herein are also configured to determine an altitude of the device in response to receiving the geolocation signals. The GPS receiver 180 of the personal electronic device 104 is able to determine the location of the device 104 on the Earth as well as the altitude of the device 104. In another embodiment, a separate processor apparatus is in communication with the GPS receiver 180, receives the raw GPS data and runs at least one application configured to determine the current position of the device 104, determine an altitude, determine distance travelled, etc.

The data server 128 as shown in FIG. 1 is electrically connected to the Internet 120 and to the remote computer 124. The data server 128 includes a memory 132 and is configured to provide data from the memory 132 to corresponding client devices such as the personal electronic device 104. The data server 128 is also configured to receive data from the personal electronic device 104 or the sensor assembly 106, including activity data, and to store the received data in the memory 132 as user data 278 (FIG. 1). Alternatively, a separate storage device may be provided. In one embodiment, the data server 128 is configured to receive requests from at least one of the personal electronic device 104 and the remote computer 124 through the Internet 120 and then to electrically transmit the user data 278 from the memory 132 to the personal electronic device 104 or the remote computer 124 via the Internet 120 and the cellular network 116.

The remote computer 124 is a computer device that is in data communication with the Internet 120 and the data server 128. The remote computer 124, in at least one embodiment, is a client of the data server 128 that is used to manage and configure the data, such as the user data 278, stored in the memory 132. The remote computer 124 is also usable to manage and configure the data stored in the memory 192 and the memory 250. Because the remote computer 124 is configured for communication via the Internet 120, it will be recognized that data may be shared between the remote computer 124 and various other components of the activity tracking system, such as the personal electronics device 104 and the sensor assembly 106. Moreover, it will be recognized that processing described herein as occurring at one location (e.g., using the controller 196 of the personal electronic device 104) may alternatively occur at one or more other locations (e.g., using the remote computer 124 or the sensor assembly 106).

In operation, the activity tracking system 100 is configured to verify the integrity of an activity type associated with activity data collected, generated, and/or logged by an activity tracking device during a workout or other activity being performed by the user. The term "activity tracking device" may be used herein to refer to either a device configured to generate activity data, such as the personal electronic device 104, the sensor assembly 106, or other device. The term "activity data" refers to data that may be collected as a user performs a workout or other activity. Thus, the term "activity data" may include, but is not limited to, the speed data 204, the altitude data 206, the sensor altitude data 210, the heart rate data 258, the respiratory data 260, the motion data 218, and/or the temperature data 262. Activity data collected by the system is associated with at least one activity type. The term "activity type" refers to any of various activities that may be performed by a user and associated with the activity data. Accordingly, the "activity type" may include running, walking, swimming, biking/cycling, or any of various other types of activities that may be performed by a user.

Figure 4:
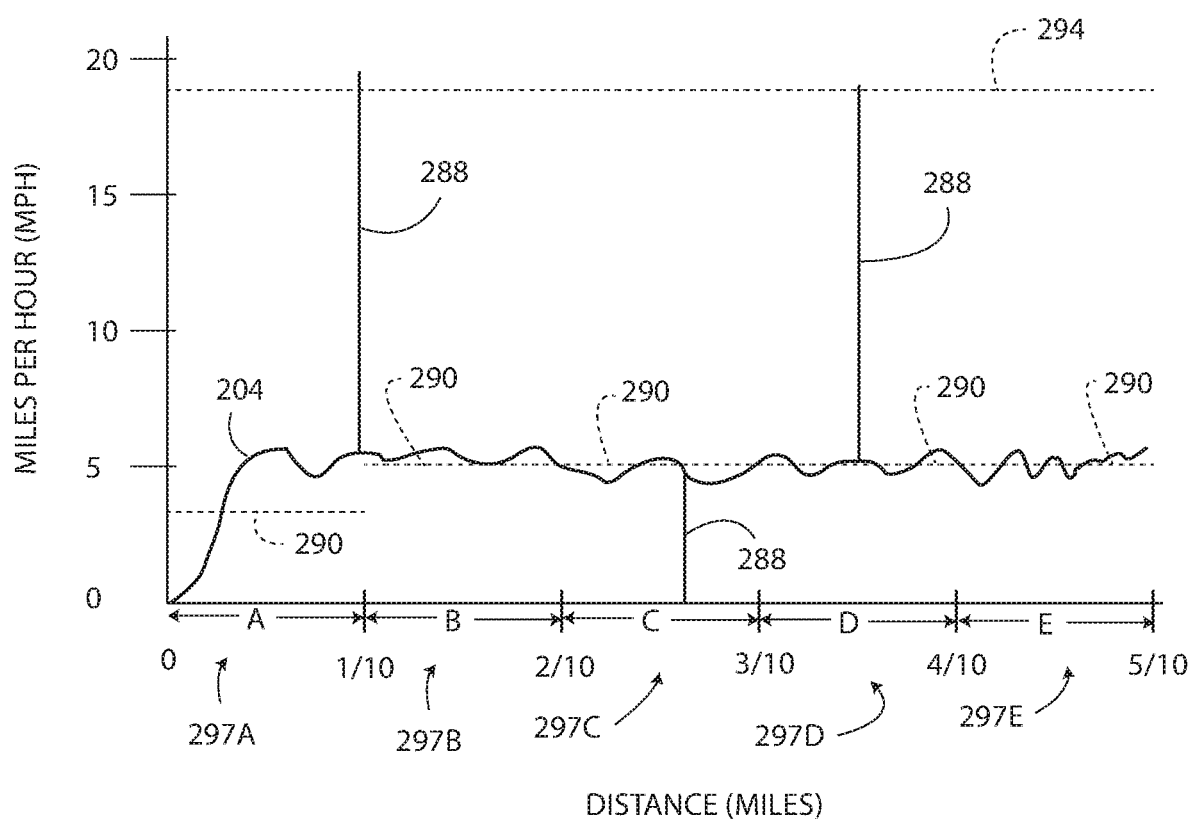
FIG. 4 is a plot of exemplary speed data verses time, the speed data generated by the activity tracking device of FIG. 1.
Figure 5:
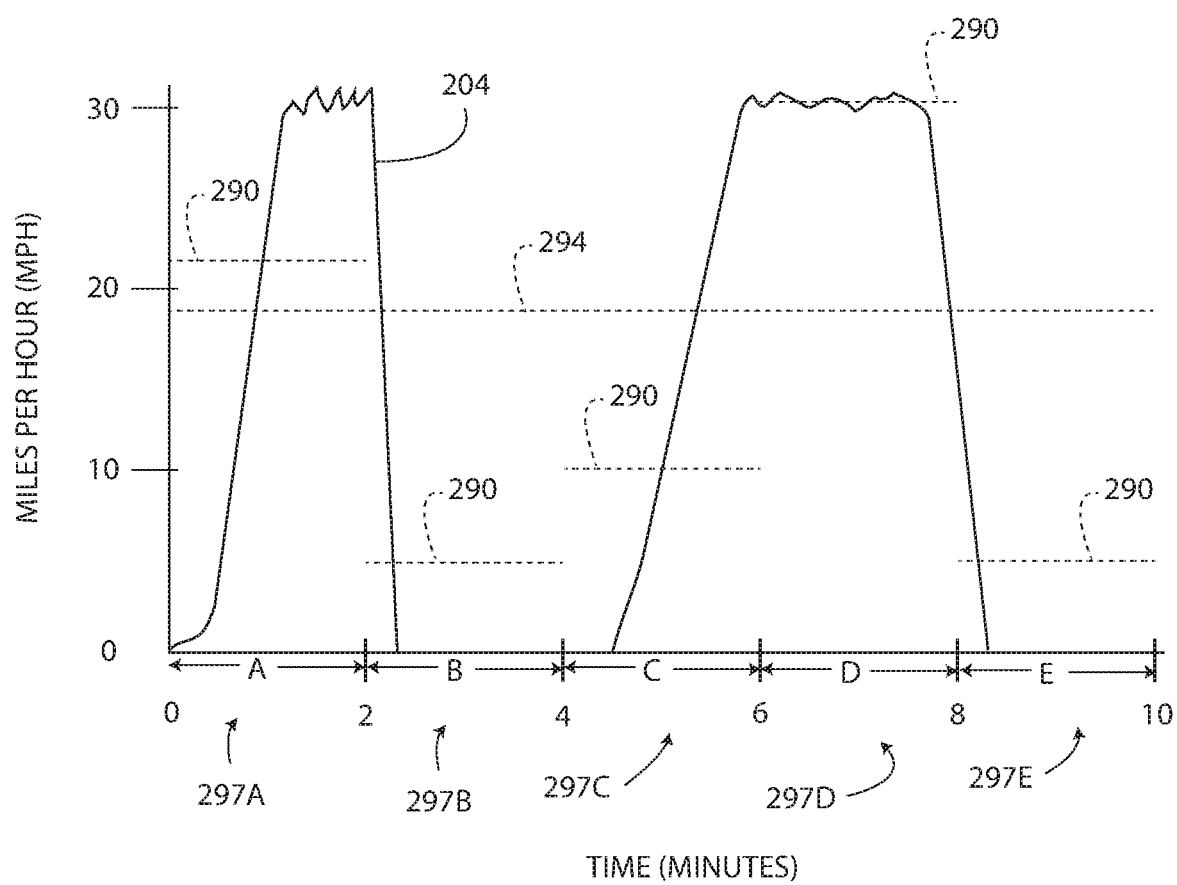
FIG. 5 is plot of another exemplary speed data verses time, the speed data generated by the activity tracking device of FIG. 1.

In one embodiment, the activity tracking system 100 is configured to verify that the activity data is properly associated with a particular activity type or configured to automatically determine an activity type most closely associated with the activity data. The activity tracking system 100 is further configured to identify activity data that was most likely not generated by the user, or was most likely not generated as a result of the physical efforts and abilities of the user. For example, the activity tracking system 100 is configured to determine that the speed data 204 plotted in FIG. 4 is representative of a user that is running. The activity tracking system 100 is also configured to determine that the speed data 204 plotted in FIG. 5 is not representative of a user that is running, and instead is representative of a user engaged in some other activity, such as riding in an automobile or some other non-athletic activity. One exemplary embodiment of the verification process used by the activity tracking system 100 is described below with further reference to FIGS. 4 and 5.

FIG. 4 shows exemplary activity data in the form of speed data 204 generated by an activity tracking device during a user workout. As shown in FIG. 4, the speed data 204 is representative of the speed of the user as determined by the GPS receiver 180 and/or the personal electronic device 104 over a duration of approximately ten minutes. Beginning from the zero minute mark, the user gradually accelerates to a speed of approximately five miles per hour (5.0 mph). The user's average speed is about five miles per hour over the duration of the activity extending from the two minute mark to the ten minute mark. The speed data 204 includes three anomalies 288, two of which indicate that the speed of the user is greater than twenty miles per hour for less than 0.001 seconds, and one of which indicates that the speed of the user is zero for less than 0.001 seconds. The GPS 288 are typical of speed data 204 and, as described below, do not impact the integrity of the speed data 204.

In verifying the integrity of the speed data 204 plotted in FIG. 4, the controller 196 determines an average speed 290 of the user each time a predetermined time period elapses. For example, in FIG. 4 each of the predetermined time periods 297A-E is two minutes. Accordingly, each time one of the predetermined time periods 297A-E elapses, the controller 196 determines the average speed 290 of the user over the duration of the previous two minutes. FIG. 4 plots the instantaneous speed data 204 extending over five predetermined time periods 297A-E. FIG. 4 also shows an average speed 290 for each time period. For predetermined time period 297A the average speed 290 is about 3.8 miles per hour. For each of predetermined time periods 297B-297E, the average speed 290 is about 5.0 miles per hour. The term "average" as used herein may refer to any number of different numbers expressing a typical value in a set of data, such as the mode, the median, the mean, or other normalized values. Moreover, the "average speed" of a user over a time period of time may be calculated in any number of different ways. For example, in at least one embodiment, the average speed of a user for a period of time may be determined by taking a number of speed values within the period of time (which may be referred to herein as "instantaneous speed values" because they are determined over relatively short distances or time periods) and then determining an average speed of the user for the period of time based on an average of those instantaneous speed values. However, in another embodiment, the average speed of the user for a period of time may be determined by simply calculating a total distance travelled between the starting and ending positions of the user during the period of time (e.g., 0.20 miles from a first point to a second point), and then dividing the total distance travelled by the time period (e.g. 0.033 hours) to arrive at an average speed over the period of time (e.g., 0.15/0.033=6 mph).

As noted previously, the speed data 204 of FIG. 4 includes a number of anomalies 288. However, in predetermined time periods 297B and 297E, the anomalies 288 do not have a practical effect on the calculated average speed 290, because the duration of predetermined time period 297B, 297E is much greater than the time duration in which the anomalies 288 occur. Accordingly, the anomalies 288 do not significantly affect the average speeds 290 determined by the controller 196 and therefore do not affect the verification process. Moreover, in some embodiments, the controller 196 is configured to filter out the anomalies 288. For example, the controller 196 is configured to discard all instantaneous speeds that are greater than some predetermined threshold (e.g., greater than thirty miles per hour (30 mph)). It is noted that a different procedure will apply to such speeds (i.e., above a threshold which continue over a longer duration).

After the controller 196 determines the average speed 290 of the user for each predetermined time period 297, the controller 196 compares each average speed 290 to a threshold average speed. The threshold average speed is based on the activity type associated with the activity data. For example, in the embodiment of FIG. 5, the activity type is running and the threshold average speed 294 is eighteen miles per hour (18.0 mph). The threshold average speed 294 is selected as a speed that a user is unlikely or unable to attain for a particular activity type being performed by the user over the duration of the predetermined time period 297. For example, very few (if any) users of the activity tracking system 100 would be able to attain an average speed of greater than or equal to eighteen miles per hour (18.0 mph) while running for a two minute time period. Thus, in the example of FIG. 4, the controller 196 compares the average speeds 290 (3.8 mph and 5.0 mph) of each predetermined time period 297A-E to the threshold average speed 294 (18.0 mph). If the controller 196 determines that the average speed 290 of each predetermined time period 297 is less than the threshold average speed 294, then the controller 196 determines that the speed data 204 (i.e. the activity data associated with this activity) is verified. In FIG. 4, the activity data (i.e. speed data 204) is verified because each of the average speeds 290 is less than the threshold average speed 294. However, if any one of the average speeds 290 is greater than the threshold average speed 294, then the controller 196 determines that all or a portion of the speed data 204 is not verified (or "unverified").

In a further embodiment, the threshold average speed 294 for each activity type (e.g., "running") may be an individualized threshold speed that is determined based on the user's past activity data. For example, if a particular user has generated activity data while running which indicates that the user is capable of running faster than a first speed (e.g., the user can run faster than ten mph), but has never run faster than second speed (e.g., the user has never run twelve miles per hour over a given time period), then the controller 196 may determine the threshold average speed 294 for the user is greater than the first speed, but equal to or slightly less than the second speed (e.g., eleven or twelve mph). This second speed is a suitable threshold average speed 294, because the user is unlikely to attain an average speed in excess of a speed that the user has never attained based on previous activity data. According to another example, if a particular user has generated activity data while running indicating an average speed of five miles per hour (5.0 mph), then the controller 196 may determine the threshold average speed 294 to be double the average speed (i.e. ten miles per hour). Any other parameter based on the user's past activity data may be used to configure the threshold average speed 294 for a particular activity type, with the goal being to identify a speed that the user unable or is very unlikely to attain as an average speed over the duration of the predetermined time period 297A-E. If the activity data indicates that the user's average speed for each period of time is less than the threshold average speed for the user, the activity data may be deemed verified. On the other hand, if the activity data indicates that the user's average speed for any one time period is greater than the threshold average speed for the user, the activity data may be deemed unverified.

As explained above, the activity data of FIG. 4 is verified activity data. Activity data that is "verified" was very likely generated as a result of the user's physical efforts and abilities exerted while performing an activity that is the same as the activity type associated with the activity data (i.e. running or walking in FIG. 4). Activity data that is "unverified" or "not verified" was very likely not generated while performing an activity that is the same as the activity type associated with the activity data, and was likely generated while performing some other activity type. Thus, unverified activity data is not likely to have been generated from the user's own physical efforts while performing the corresponding activity type. Unverified activity data may be generated in any of various ways such as in response to user input errors or poor GPS reception.

Unverified activity data may also be generated in response to the user intentionally or unintentionally indicating to the personal electronic device 104 that the corresponding activity type is one activity and then performing a different activity. For example, the user may select the activity type for a workout as "running" and then, intentionally or unintentionally, ride an automobile, ride a bicycle, or perform some other activity that is not the selected activity type for the workout. Accordingly, unverified data may be typically generated as a result of a nonathletic pursuit or a pursuit that is unrelated to the selected activity type. Determining whether activity data is verified or not verified may be performed in any number of different ways. In the example of FIG. 4 activity data is evaluated and determined to be "verified" because the average speed 290 of each predetermined time period 297A-E is less than the threshold average speed 294 associated with the indicated activity type (i.e., "running"). Various activity types that the activity tracking system 100 is configured to verify may be referred to herein as verifiable activities and/or verifiable activity types.

With reference now to FIG. 5, unverified activity data, including different speed data 204, are plotted over a period of time. The activity data is associated with the activity type "running," and the alleged running event occurred over a duration of ten minutes. FIG. 5 illustrates five predetermined time periods 297A-E each of two minutes. The average speed 290 during predetermined time period 297A is about 22 miles per hour (22.0 mph). The average speed 290 during predetermined time periods 297B and 297E is about six miles per hour (6.0 mph). The average speed 290 during predetermined time period 297C is about ten miles per hour (10 mph), and the average speed 290 during predetermined time period 297D is about thirty miles per hour (30 mph). The controller 196 determines that the activity data is unverified because the average speeds 290 of predetermined time periods 297A and 297D are above the exemplary threshold average speed 294 of 18 miles per hour (18 mph) for the running activity type. Thus, the activity data (i.e.

speed data 204) plotted in FIG. 5 is determined to be unverified, because at least one average speed 290 exceeds the threshold average speed 294.

Since the activity data of FIG. 5 is unverified, the controller 196 determines that the activity type associated with the activity data is an activity type other than the performed activity by the user at the time the activity data was generated. In the exemplary embodiment of FIG. 5, the controller determines that there is a high likelihood that the activity data was not generated in response to a bipedal activity of the user (e.g., running), and instead was generated, at least in part, during some other type of activity.

The activity data of FIG. 5 illustrates that the duration of the predetermined time period 297A-E contributes to determining if the activity data is verifiable. For example, if the predetermined time period was ten minutes instead of two minutes, then only a single predetermined time period would be shown in FIG. 5 and all of the speed data 204 of FIG. 5 would be included in the single predetermined time period. According to such an example, the average speed of the speed data 204 in FIG. 5 for the ten minute predetermined time period is about 14 miles per hour (14.0 mph), which is less than the threshold average speed 294 for a running user. This is a misleading result because the speed data 204, which includes data points at greater than 30 mph, could not have been generated by a running user. Accordingly, this example illustrates that in some embodiments, a ten minute predetermined time period may be too long to accurately verify the activity data of a running user.

The controller 196 selects the predetermined time period 297A-E to correspond to an optimum duration of time for verification purposes for a particular activity type without being impacted by the anomalies 288 and other irregularities. Typically, athletic pursuits having a lower average speed correspond to shorter predetermined time periods 297A-E, and athletic pursuits having a comparatively higher average speed correspond to longer predetermined time periods 297A-E. For example, for an activity type such as running that has a typical average speed of six miles per hour (6.0 mph) a predetermined time period of 10 minutes is typically too long to accurately verify the activity data, because the speed data 204 from nonathletic pursuits, such as riding in an automobile, may have an average speed that is less than the threshold average speed. Whereas, for an activity type such as running, a predetermined time period of ten seconds is too short to accurately verify the activity data, because the anomalies 288 and other irregularities may affect the calculated average speeds. Typically, a predetermined time period 297A-E of thirty seconds to three minutes is suitable for an activity type such as running, walking, hiking, jogging, or the like.

Data relating to a verified activity may be utilized in subsequent determinations of the verifiable range of data collected for the same activity. In other words, the system is configured to "learn" from collected data to improve future comparisons.

In the foregoing examples of FIGS. 4 and 5, verification of activity data includes determination of an average speeds for the user over periods of time, and determination of average speed is based on activity data collected over a number of time periods 297A-E, wherein each time period is a predetermined length of time (e.g., two minutes). However, it will be recognized that in other embodiments, the average speed may be calculated differently. For example, instead of determining the average speed after each predetermined time period 297A-E, the controller 197 may be configured to determine the average speed after the user travels a predetermined distance. An exemplary predetermined distance may be approximately 0.1 miles. Moreover, although verification of the activity data in the example of FIGS. 4 and 5 is made with reference to determination of average speeds, it will be recognized that other parameters may be used to verify activity data. For example, as explained in further detail below with reference to FIGS. 6, 7, 8A and 8B, heart rate data or other data generated by an activity tracking device may also be used to verify activity data associated with a particular activity type.

Figure 6A:
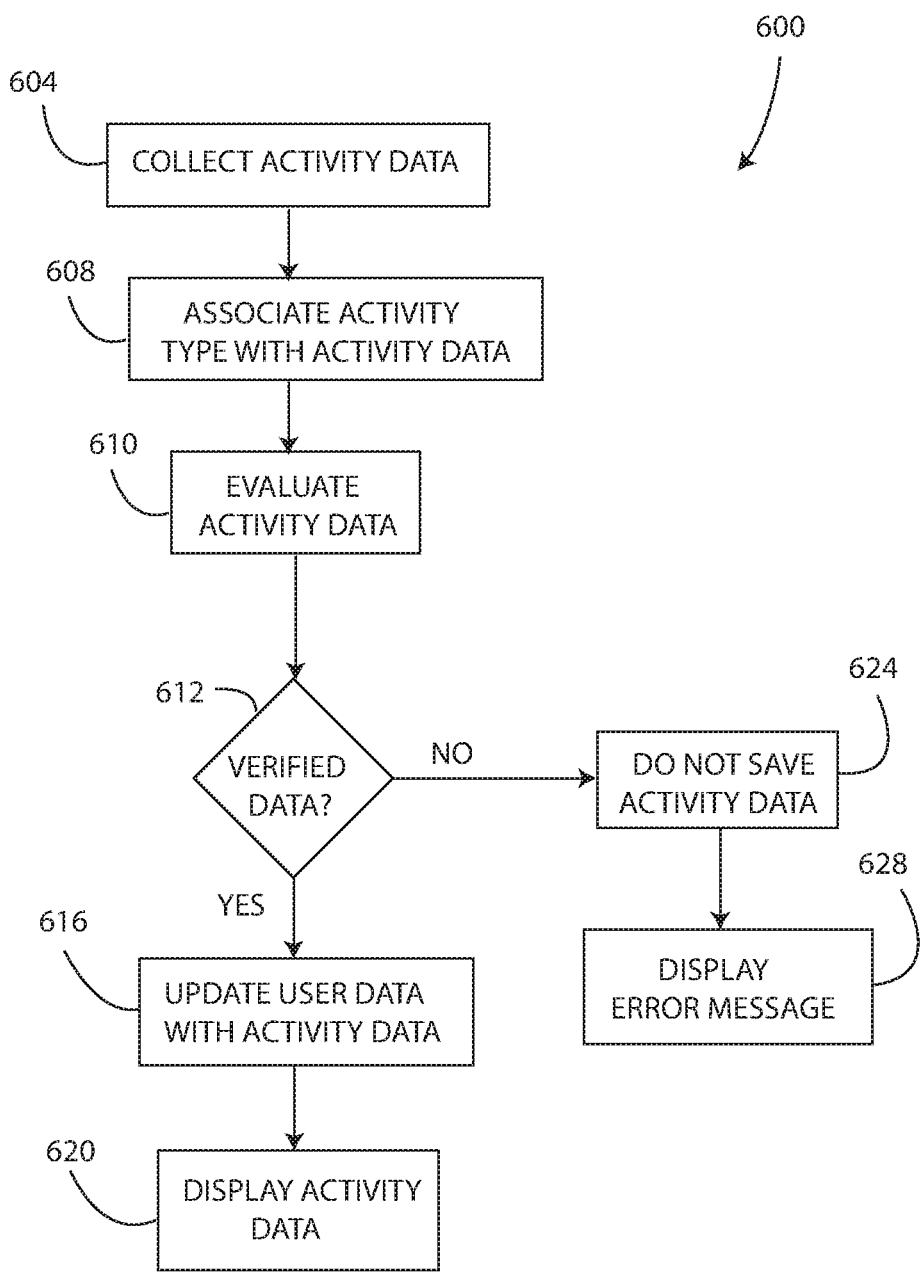
FIG. 6A is a flowchart illustrating an exemplary method for operating the activity tracking system of FIG. 1.
Figure 6B:
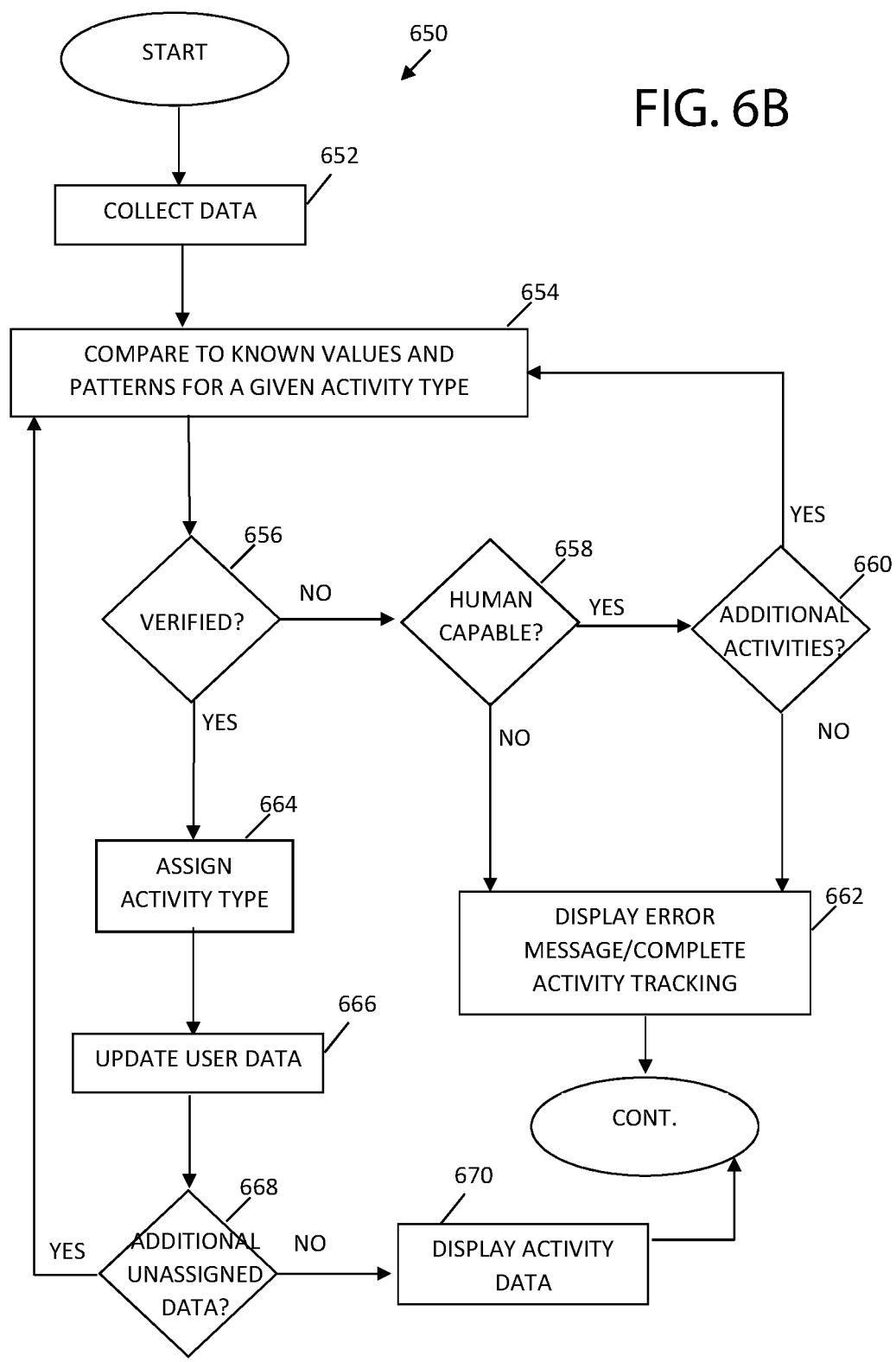
FIG. 6B is a flowchart illustrating another exemplary method for operating the activity tracking system of FIG. 1.

With reference now to FIGS. 6A and 6B, methods 600 and 650 describe how the activity data is associated with an activity type and how the activity tracking system 100 verifies the integrity of the activity data. In the description of the methods 600 and 650, statements that a method is performing some task or function refers to a controller or general purpose processor executing programmed instructions stored in non-transitory computer readable storage media operatively connected to the controller or processor to manipulate data or to operate one or more components in the activity tracking system 100 to perform the task or function. Particularly, the processor circuitry/logic of the controller 196 of the personal electronic device 104 above can be such a controller or processor. Alternatively, the controller 196 can be implemented with more than one processor and associated circuitry and components, each of which is configured to form one or more tasks or functions described herein. Additionally, the steps of the methods 600 and 650 may be performed in any feasible chronological order, regardless of the order shown in the figures or the order in which the steps are described.

Referring now to FIG. 6A, an exemplary method 600 for operating the activity tracking system of FIG. 1 is given. The method 600 is utilized in the instance the user has manually selected an activity type, as discussed herein. Additional methods are provided in the instance the user has not or does not select an activity type (see FIG. 6B).

As shown, per step 604, activity data is collected. The activity data may comprise any one of a plurality of types of data which may be measured via an activity sensor. For example, the activity data may comprise step data, heart rate data, respiration data, speed data, ambient temperature and/or body temperature, etc. Although not discussed herein, various other physiological and environmental aspects may be reviewed according to the methods discussed herein.

Next per step 608, the activity data is associated to an activity type. In one embodiment, the association is based on a manual entry or selection of an activity type by the user. For example, a list of available activity types may be provided to the user; the user reviews the list and determines which of the activity types is associated with the performed activity. It is also appreciated that in another embodiment, the user may select the activity type before the activity data is collected (i.e., before beginning the workout).

The collected activity data is evaluated at step 610 to determine whether the patterns and values thereof correspond generally with the predetermined range of values expected of the selected activity. It is during this evaluation that the system determines whether the data is verified (step 612). That is, the data is compared to typical activity data for the same activity type. When it is found that the collected data is within a predetermined threshold or range of the typical activity data for that same activity type, the data is deemed to be verified. When it is found that the data is outside of the predetermined threshold or range, the data is determined to not be verified. The typical activity data may comprise average data across multiple users and/or average data for that particular user, as discussed elsewhere herein. Additionally, it is noted that the threshold and/or range may comprise a number or range selected by a network operator or automatically selected based on activity type and/or data type.

Verified data is at step 616 provided to one or more network servers as an update to the user's activity data in one embodiment. That is, in the instance that the typical activity data to which newly collected activity data is compared comprises average data for the particular user, the newly verified activity data may be used to update that average. In other instances, the verified activity data may simply be stored in association with the user. Finally, the activity data, once verified, is displayed (step 620).

In the instance the activity data cannot be verified (i.e., falls outside of the given range and/or threshold for activity data of that activity type), the activity data is not saved (step 624) and an error message is displayed to the user (step 628). In another embodiment, the inability to verify the data may also trigger the system to discontinue activity tracking.

It is appreciated that the herein described method 600 may be applied to each aspect or type of activity data collected (e.g., heart rate data, step data, speed data, etc.). The verification of a predetermined number of these data being necessary in order to verify the data as being of the stated activity type. For example, it may be determined by the network operator that verification of heart rate and speed data are required in order to verify data as the activity type: running. Accordingly, if additional data is collected, such as temperature, it may be unevaluated and/or the results of an evaluation may be irrelevant to the determination of the data as running data. In other examples, a certain number or percentage of the collected data may be required to verify the data as belonging to the selected activity (e.g., 4 out of 5 collected data aspects must be verified, etc.).

Figure 7:
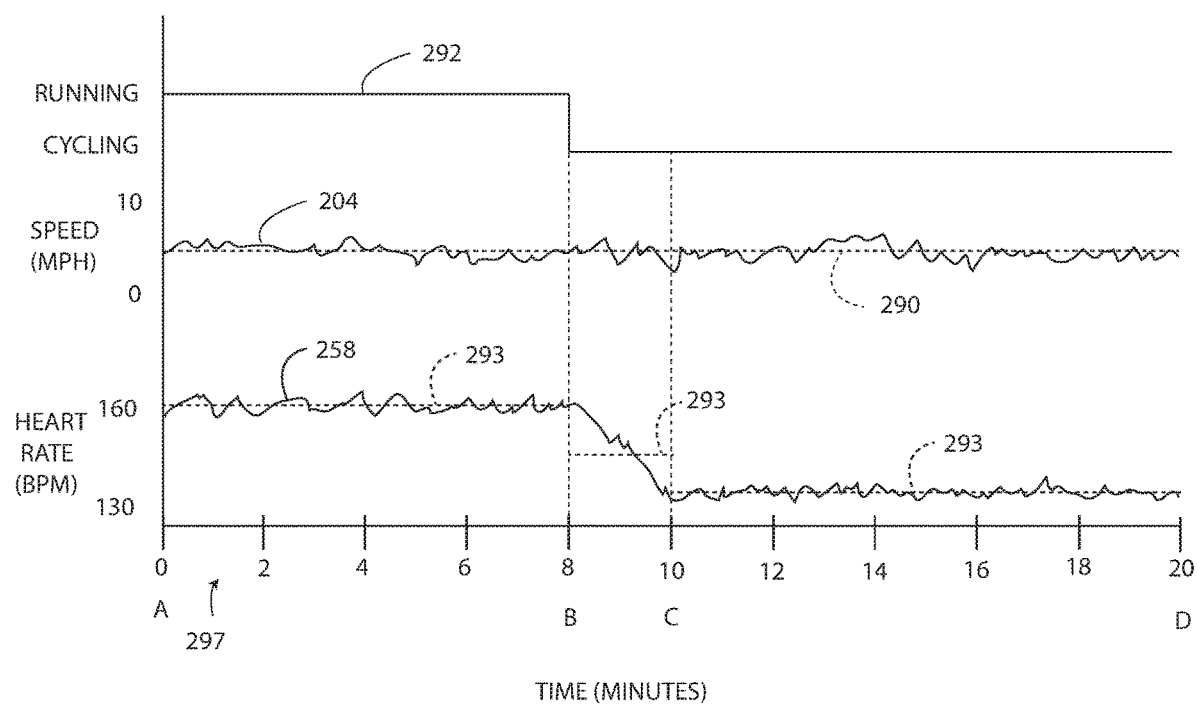
FIG. 7 is a plot of exemplary activity type data, speed data, and heart rate data verses time, the data generated by the activity tracking device of FIG. 1.

The method 600 is presented below with reference to the specific activity data shown in FIGS. 7, 8A and 8B. A brief description of the activity data shown in FIGS. 7, 8A, and 8B is provided prior to the description of the method 600 of FIG. 6A in order to introduce the reader to the activity data. The method of FIG. 6A is then described referencing the exemplary data of FIGS. 7, 8A and 8B. While the method 600 is generally described as being performed using the controller 196 of the personal electronics device 104, it will be recognized that the processing may also occur using any of various other controllers in the activity tracking system 100. For example, processing for the method 600 may additionally or alternatively be performed by e.g., the remote computer 124.

FIG. 7 shows activity data including speed data 204 and heart rate data 258 generated over a twenty minute workout session. FIG. 7 also shows activity type data 292 corresponding to the type of activity being performed by the user as the activity data is generated. In FIG. 7, the activity type data is "running" from zero to eight minutes and is "cycling" from eight minutes to twenty minutes. The speed data 204 indicates that the average speed 290 of the user is generally the same for each predetermined time period 297 while running and cycling; however, the heart rate data 258 indicates a noticeable decline in average heart rate 293 when the user switches from running to cycling. The decline in average heart rate generally occurs from point B to point C.

FIGS. 8A and 8B illustrate individualized data sets 296, 298 for the user (i.e., the user that generated the activity data of FIG. 7). In at least one embodiment, the individualized data sets 296, 298 provide historical heart rate averages for the user based on previous activity data generated by the system 100. Alternatively, the training or default data may be entered manually by a network operator. The data set 296 of FIG. 8A shows user average heart rate data corresponding to the running activity type. The data set 298 in FIG. 8B includes user average heart rate data corresponding to the cycling activity type. The data sets 296, 298 include four columns of data, each of which is associated with a different speed range. Accordingly, based on the data set 296, the user typically has an average heart rate (taken over the course of the predetermined time period 297A-E) of 135 beats per minute (135 bpm) when the user is running or walking at a speed of 2-4 miles per hour. The user has a higher average heart rate of 160 beats per minute (160 bpm) when running or walking at a speed of 4-6 miles per hour. When cycling at greater than six miles per hour (6.0 mph) the user is expected to have an average heart rate of about 150 beats per minute (150 bpm) over the course of the predetermined time period 297 (FIG. 7). In one embodiment, the data contained in the individualized data sets 296, 298 corresponds to the predetermined range of values assigned to the corresponding activity type.

FIGS. 8A and 8B, also illustrate a tolerance range that is established by the controller 196. In the example data sets 296, 298, the controller 196 has established a plus or minus ten percent (±10%) tolerance band around each average heart rate value. Accordingly, for a given average speed, if the measured average heart rate falls within the tolerance band of the expected average heart rate for that average speed, then the user is likely performing the corresponding activity. However, if, the measured average heart rate is outside of the tolerance band of the expected average heart rate, then the user is likely not performing the corresponding activity. The controller 196 is configurable for any desired tolerance band. Typical tolerance bands range from plus or minus five percent (±5%) to plus or minus twenty percent (±20%).

In the above-described embodiment, the data of the data sets 296, 298 are determined by the controller 196 or the remote computer 124 by analyzing previous sets of activity data of the user as well as physical characteristics of the user such as sex, weight, height, age, and general physical fitness level. However, in at least one alternative embodiment, the data of the data sets 296, 298 may be input manually by an operator using the input unit 172. In yet another alternative embodiment, the data of the data sets 296, 298 may be provided based on averages for user based on the user's profile data, such as sex, weight, height, age, general physical fitness level, and other relevant characteristics. Moreover, in at least one embodiment, if a user does not have a corresponding personalized data set 296, 298, then the controller 196 initially uses a generalized data set(s) (e.g., averaged across multiple other users) that is based on the user's sex, weight, height, age, general physical fitness level, and other relevant characteristics. Then, as the user logs activity data, the generalized data set(s) is updated and becomes the user's individualized data set(s). In one embodiment, the predetermined range of values associated with an activity type is determined based on the data in the generalized data set.

A detailed example of the method 600 of FIG. 6A is now discussed with reference to the activity data of FIG. 7 and the data sets 296, 298 of FIGS. 8A and 8B. As shown in block 604, activity tracking devices collect activity data during a workout or other activity performed by a user of the activity tracking system 100. In the example of FIG. 7, the activity data includes the speed data 204 (e.g., provided by a smartphone), and the heart rate data 258 is generated/ detected by the electrodes 236 of the sensor assembly 106 (e.g., a heart rate sensor on a chest strap).

In block 608, the activity tracking system 100 associates an activity type with the activity data. In this example, at the beginning of the workout, the user manipulates the input unit 172 to indicate that a "run" activity type is about to occur in association with a workout. Accordingly, all activity data generated by the activity tracking system 10 is associated with a "run" activity type until the user indicates a new activity type is input by the user or the workout terminates. In the embodiment of FIG. 7, the "run" activity type is associated with the activity data between points A and B. However, at point B, the user again manipulates the input unit 172 to indicate that all future data during the workout should be associated with the "cycling" activity type.

Once the activity data is associated with an activity type, the method 600 moves to step 610 and the activity data is evaluated. In this example, when evaluating the activity data of FIG. 7 between points A and B, the controller 196 compares the activity data (i.e. the speed data 204 and the heart rate data 258 of FIG. 7) to the data of the data set 296 shown in FIG. 8A which corresponds to the "running" activity type associated with the activity data between points A and B. It will be noted that if the activity data between points A and B of FIG. 7 was associated with the a different activity type, the controller 196 would compare the activity data to data of a data set for that activity type (see e.g., FIG. 8B).

During each predetermined time period 297 from point A to point B in FIG. 7, the measured average heart rate 293 of the user is about 165 beats per minute (165 bpm), and the measured average speed 290 of the user is about 5.2 miles per hour (5.2 mph). Based on the measured average speed of 5.2 miles per hour, the data set of FIG. 8A indicates that the average heart rate should be about 160 bpm, or within a plus or minus ten percent tolerance band thereof (i.e., 144 bpm-176 bpm). Since the measured average heart rate 293 of 165 bpm is within the range of 144-176 beats per minute for each predetermined time period 297 between points A and B, the controller 196 determines that a "match" has occurred and that the user is/was running or walking during the period extending from point A to point B. In this manner, the controller 196 has evaluated the activity data (step 610) and confirmed that the activity type "running" that was input by the user (see activity type data 292 of FIG. 7) was/is accurate (and therefore verified activity data, step 612), because, according to the evaluated activity data, the user was very likely running during the time extending between point A and point B.

Next, continuing with the evaluation of the activity data in step 610, the controller 196 next evaluates the activity data between points B and C of FIG. 7. As noted previously, at point B, the user noted a change in activity type from "running" to "cycling." Accordingly, all activity data in FIG. 7 after point B is associated with the "cycling" activity type. A change in average heart rate 293 (either up or down) and/or a change in average speed 290 (either up or down) is typically an indication that the user has changed activity types. This tendency is shown in the activity data of FIG. 7 between points B and C. Specifically, from point B to point C, the user's average heart rate 293 transitions from about 165 bpm at point B to about 133 bmp at point C (for an average of about 140 bpm for the period), even though the user maintains an average speed of about 5.2 mph over this period. When evaluating the activity data between points B and C of FIG. 7, the controller 196 compares the activity data (i.e. the speed data 204 and the heart rate data 258 of FIG. 7) to the data of the data set 296 shown in FIG. 8B which corresponds to the "cycling" activity type associated with the activity data between points B and C. The controller 196 processes the data set 296 to determine that the user is very likely cycling (e.g., verifies the data per step 612), because with an average measured speed of 5.2 mph, the user's heart rate should be between 117 mph and 143 mph (see column 2 of FIG. 8.2), and the user's average heart rate of 140 during the period from point B to point C falls within this range. Thus, another "match" has occurred.

Next, the controller 196 continues to evaluate the activity data associated with the predetermined time periods 297 by processing the activity data between point C and point D of FIG. 7. In particular, from point C to point D, the average measured heart rate 293 is about 133 beats per minute and the measured average speed 290 is still about 5.2 miles per hour. Comparing this activity data to the individualized data set 298 of FIG. 8B for the "cycling" activity type, the controller 196 determines that it is very likely that the user is cycling. In particular, because the user's average speed is 5.2 mph, and because the measured average heart rate of about 133 bpm is well within the tolerance band of average heart rates (i.e. 117-143) for this speed when cycling (see column 2 of FIG. 8B), the activity data is verified.

Therefore, the controller 196 has verified that the activity data from point A to point B is properly associated with the "running" activity type by comparing the user's measured average speed 290 and measured average heart rate 293 to the data of the individualized data set 296 of FIG. 8A. Similarly, the controller 196 verified that the activity data from point B to point D in FIG. 7 is properly associated with the "cycling" data type by comparing the user's measured average speed 290 and measured average heart rate 293 to the data of the individualized data sets 298 of FIG. 8B. In other words, the activity data is verified by comparing the activity data to a normalized data set corresponding to an associated activity type (e.g., the individualized data sets of FIGS. 8A and 8B, respectively corresponding to cycling and running activity types), and evaluating whether the activity data matches the normalized data set (e.g., does the activity data fit within the tolerance parameters of the normalized data set). Activity data may be determined to be not verified (or suspect) if a comparison of the activity data to the normalized data set for the activity type does not match the normalized data set. Furthermore, although evaluation of the activity data and associated verification of such data has been described with respect to the exemplary activity data in FIG. 7 and the associated individualized data sets of FIGS. 8A and 8B, it will be recognized that other methods may be used to evaluate the activity data, such as comparing the activity data to threshold data associated with a particular activity type. Additionally, although verification of activity data has been explained in the foregoing examples using activity data in the form of speed data and/or heart rate data, it will be recognized that one or more of any of various types of activity data may be used in the verification process (e.g., the speed data 204, the motion data 218, the heart rate data 258, the respiratory data 260, the altitude data 206, the temperature data 262, or any various other types of activity data).

Continuing now with the method 600 of FIG. 6A, after evaluating the activity data, the method 600 continues in block 612, and the controller 196 determines whether the activity data 292 is verified or unverified. If the activity data was not verified data, the method continues to block 624. If the activity data was verified data, the method continues to block 616.

If the activity data is verified data, in block 616 the controller 196 updates the user data 278 (including the data sets 296, 298) stored in the memory 132 with the verified activity data. For example, the user data 278 is updated to tally the total verified distance and time that was run and cycled by the user. Also, the data server 128 or the remote computer 124 re-computes the average heart rates stored in the data sets 296, 289 for each of the speed ranges based on the updated data. This causes the average heart rates of the data sets 296, 298 to accurately reflect the user's unique physiology based on the user's current fitness level. For example, as the user becomes more fit, the average heart rates of the data sets 296, 298 will typically trend downward for each speed range as the user's heart becomes more efficient. Whereas, if the user fails to exercise regularly, the average heart rates of the data sets 296, 298 may trend upward, thereby indicating that the user has become less physically fit. By adjusting the average heart rates of the data set 296, 298 with the verified activity data, the activity tracking system 100 is able to more accurately determine the activity type data 292 for subsequently collected data. Similar logic may also be applied to other activity ranges.

After updating the user data in block 616, the method 600 continues to block 620, and the controller 196 displays the activity data and other data on the display 168 of the personal electronic device 104 to be viewed by the user.

In block 624 of the method 600, if the controller 196 determines that the activity data was not verified for any one of the predetermined time periods 297, then the controller 196 does not upload the activity data to the memory 132 and the activity data does not become associated with the user data 278 or the data sets 296, 298. In this way, the method 600 prevents the user from corrupting the user data 278 and the data sets 296, 298. Specifically, if the average heart rates of the data sets 296, 298 were recomputed with unverified activity data, then the average heart rates would not be representative of the user's unique physiology, and the activity tracking system 100 would be less likely to determine accurately and automatically the activity type data 292 for subsequently collected data.

Next, in block 628 of the method 600, the controller 196 configures the display 168 to display an error message or other type of message to alert the user that the activity data has not been verified.

Optionally, when data cannot be verified and/or an activity type cannot be verified (because there are not enough data matches), then the system may recommend a different activity type via the mechanisms discussed in FIG. 6B below and/or may enable the user to select a different activity type.

Referring now to FIG. 6B, another exemplary method 650 for operating the activity tracking system of FIG. 1 is given. The method 650 is utilized in the instance the user not has manually selected an activity type, but rather the system will determine one automatically based on the data collected, as discussed herein.

As shown, per step 652 of the method, activity data is collected. As noted elsewhere herein, the activity data may comprise heart rate data, step data, distance data, altitude data, temperature data, etc., as well as any other measurable physiological and/or environmental factors. Next, the collected data is compared to known values and patterns for a given activity type (step 654). In one embodiment the activity type may be manually selected by the user, or alternatively may be automatically selected by the system. In one variant, the system may access a list of possible activities, which are individually applied as discussed herein to determine the most likely activity to which the collected data corresponds. In another variant, the list of possible activities may be applied in a logical order, such as according to the frequency with which the user participates in each activity. In yet another variant, patterns in the data are first analyzed in order prioritize the list from most to least likely activity; these are then applied to the data for further scrutiny as discussed herein.

The evaluation of the data against the first one of the available activity types (and/or against the activity type selected by the user) is discussed in greater detail elsewhere herein. In one embodiment, various ones of the aspects of the collected data are compared against average or default data for a given activity type. When the collected data is within a given threshold or range of the typical data, the data is determined to be verified (step 656). When the collected data is outside the range or threshold, the data is not verified (step 656).

In the instance that the data is not verified, then the method 650 continues to step 658 where it is determined whether a human is physically capable of generating the data. For example, if the ratio of heart rate to speed data is very high, it is clear that a human would not be generating the data (rather they are likely in a motorized vehicle). When this occurs, per 662, an error message is displayed to the user. In another embodiment, the tracking of activity data is also triggered to complete.

In the instance that the unverified data is capable of being generated by a human, then the method continues to step 660, where it is determined whether there remain any additional activities which the data has not yet been evaluated against. If there are no remaining activities, per step 662 an error message is displayed and the activity tracking is ceased. In the instance other activities remain, the method 650 re-preforms step 654 with respect to a second activity type.

In the instance the data is verified, the activity type against which the data was evaluated is assigned to the data (step 664), and the user data is updated (step 666). As noted above, the user data may be updated to individualize the activity type data against with subsequent data is evaluated in one embodiment.

Next, it is determined at step 668 whether there remains any additional unassigned data, if not (step 670) the activity data is displayed to the user. If additional data remains, the method 650 repeats to step 654 and the remaining data is evaluated.

With reference now to FIGS. 9, 10A, 10B, and 10C, in at least one exemplary embodiment the activity tracking system 100 of FIG. 1 is configured to automatically determine the activity type associated with activity data and verify the activity data according to the method of FIG. 6B. In the exemplary embodiment of FIGS. 9, 10A, 10B and 10C, the activity data includes the speed data 204, the motion data 218, the heart rate data 258, the respiratory data 260, the altitude data 206, and the temperature data 262. The processing steps exhibited by the controller 196 are described below with reference to the method 650 of the activity tracking system 100 illustrated in FIG. 6B and the data sets 314, 316, and 318 of FIGS. 10A, 10B, and 10C.

The method 650 begins with the activity tracking system 100 collecting the activity data plotted in FIG. 9, as noted in block 652 of FIG. 6B. The present example assumes only three possible activities: running, cycling, and swimming; further, the present example assumes the following activity data is collected: the speed data 204, the motion data 218, the heart rate data 258, the respiratory data 260, the altitude data 206, and the temperature data 262.

Next, the controller 196 automatically determines which of the activity type data 292 to begin evaluations against, as noted in block 654 of FIG. 6B. From point A to point B of FIG. 9, the controller 196 processes the altitude data 206 (or the sensor altitude data 210) to look for patterns therein. The system determines that the user underwent substantially no altitude change, as is consistent with a user that is swimming. Thus, the controller 196 determines that the altitude data 206 tends to show that the user is swimming or is moving on a very flat area. Accordingly, the controller 196 determines that a match has occurred. The data sets 314, 316, 318 do not include "user altitude data," since the conclusions that the controller 196 draws from the altitude data 206 are not based on the physiology of the user.

In one embodiment, when processing the altitude data 206, the controller 196 periodically derives the altitude data 206 to determine the instantaneous slope of the altitude data. The derivatives are compared to a threshold value to determine if the user is moving on a flat area or not. For example, since the altitude data 206 from point A to point B is flat the derivatives will be zero or very close to zero. Whereas, if the user is experiencing an altitude change the derivatives will include non-zero values. If all, most, or a predetermined portion of the derivatives are less than the threshold value, then the controller 196 determines that the user tends to be moving on a flat area. If all, most, or a predetermined portion of the derivatives are greater than the threshold value, then the controller 196 determines that the user is not moving on a flat area.

Next, the controller 196 processes the motion data 218. The motion data 218 is comparatively low in magnitude and lacks the rhythmic peaks 302 that are present when the user is running. Thus, the controller 196 determines that the motion data 218 also tend to show that the user is swimming from point A to point B. Accordingly, another match has occurred.

In one embodiment, the controller 196 samples the motion data to arrive at a plurality of sampled data points. Next, the controller 196 compares the sampled data points to a threshold value, and if all, most, or a predetermined portion of the sampled data points are less than the threshold value, the controller 196 determines that the user tends not to be running. Whereas, if all, most, or a predetermined portion of the sampled data points are greater than the threshold value, then the controller 196 determines that the user may be running.

Thereafter, the controller 196 processes the speed data 204 and the heart rate data 258 in conjunction with the data sets 314, 316, 318. From point A to point B, the controller 196 determines that the average speed 290 is about 3.5 miles per hour and that the average heart rate 293 is about 165 beat per minute. The running data set 314 indicates that the user is expected to have a heart rate of about 117 to 143 when moving at 3.5 miles per hour (with a 10% tolerance band). Since the measured average heart rate 293 of 165 beats per minute is outside of this window, the controller 196 determines that the heart rate data 258 and the speed data 204 tend to show that the user is not running. As a result, a match has not occurred. The cycling data set 316 indicates that the user is expected to have a heart rate of about 81 to 99 when moving at 3.5 miles per hour (with a 10% tolerance band). Since, the measured average heart rate 293 of 165 beats per minute is outside of this window, the controller 196 determines that the heart rate data 258 and the speed data 204 tend to show that the user is not cycling. As a result, a match has not occurred. Next, the controller 196 processes the swimming data set 318, which indicates that the user is expected to have a heart rate of about 153 to 187 while swimming at 3.5 miles per hour (with a 10% tolerance band). Accordingly, since the measured heart rate of 165 beats per minute is within this window, the controller 196 determines that the heart rate data 258 and the speed data 204 tend to show that the user is swimming and another match has occurred.

Additionally, the controller 196 processes the respiratory data 260 and the speed data 204 in conjunction with the data sets 314, 316, 318. From point A to point B, the average respiration rate 295 is about eighteen breaths per minute (18 bpm). The controller 196 compares the average respiration rate 295 at the average speed of 3.5 miles per hour to each data set 314, 316, 318 and determines that the average respiration rate 295 tends to show that the user is either running or swimming.

Next, the controller 196 processes the temperature data 262. The temperature data 262 is generally constant from point A to point B. When the user is swimming, the temperature sensor 244 is typically surrounded by water and thus is at least partially influenced by the temperature of the water. Accordingly, the generally constant temperature data 262 reflects the generally constant water temperature and tends to show that the user is swimming. Moreover, the temperature data 262 has a dip 306 at point B. The dip 306 in temperature is typically the result of water evaporating from the temperature sensor 244 as the user exits the pool or other body of water. Accordingly, the flat temperature data 262 terminated with a temperature dip 306 tends to show that the user is swimming. As a result, the controller 196 determines that the temperature data 262 tends to show that the user is swimming from point A to point B.

Based on the above, the controller 196 determines that activity data in FIG. 9 tends to show that the user is swimming (more so than cycling or running) from point A to point B. Thus, the controller 196 generates activity type data 292 of "swimming" from point A to point B. In is appreciated that other aspects may be evaluated and that data for other sports or activities may be provided for comparison to the collected data. In other words, the data is verified from point A to point B as swimming data (step 656). Accordingly, the activity type is assigned (step 664) and the user data is updated (step 666). In one embodiment, the controller 196 assigns the activity type to the activity data after a predetermined number of matches has occurred. For example, the controller 196 assigns the activity type to the activity data after three matches have occurred.

After processing the activity data from point A to point B, the controller 196 determines that additional activity data remains (i.e., the activity data from point B to point C), per step 668 the method 650 repeats in the same manner beginning at the evaluation step 654. Accordingly, patterns in the data are determined. First, the controller 196 processes the altitude data 206 and determines that the user underwent an altitude change of greater than 100 m. It is not a normal situation for a user to undergo such a substantial change in altitude while swimming; thus, based on the change in altitude, the controller 196 determines that the altitude data 206 tends to show that the user is not swimming from point B to point C. Next, the controller 196 processes the motion data 218 and determines that the rhythmic peaks 302 are not present; accordingly, the controller 196 determines that the motion data 218 tends to show that the user is not running. Instead, the motion data 218 are largely irregular with a few large spikes 310. The low magnitude irregular data are indicative of the user rolling over a roadway on a bicycle, and the large spikes 310 are indicative of the user hitting sizable bumps in the roadway with bicycle, for example.

Thus, the motion data 218 tends to show that the user is cycling. Next, the controller 196 compares the heart rate data 258, the respiration data 260, and the temperature data 262 to the data sets 314, 316, 318 and determines that the user is likely cycling from point B to point C. The controller 196 determines that activity data in FIG. 9 tends to show that the user is cycling more so than swimming or running from point B to point C. Thus, the controller 196 generates activity type data 292 of "cycling" from point B to point C.

The verified data (step 656) is then assigned the activity type for cycling (step 664) and the user data is updated (step 666).

Additional activity data remains for the period between point C to point D (step 668). Hence, the method 650 repeats at step 654 and the controller 196 evaluates the activity data from point C to point D in the same manner as discussed above. First, the controller 196 processes the speed data 204 and determines an average speed 290 of about six miles per hour (6.0 mph). Next, the controller 196 processes the altitude data 206 and determines that the user underwent an altitude change of at least 50 m. The controller 196 thus determines that altitude data 206 tends to show that the user is not swimming from point C to point D. Next, the controller 196 processes the motion data 218 and identifies the rhythmic peaks 302 associated with a running user. The peaks 302 correspond to a step rate of about 160 steps per minute. The running data set 314 indicates that the user is expected to have a step rate of about 144 to 176 while moving at 6.0 miles per hour (with a 10% tolerance band). Accordingly, since the measured step rate of 160 steps per minute is within this window, the controller 196 determines that the motion data 218 and the speed data 204 tend to show that the user is running. Next, the controller 196 compares the heart rate data 258, the respiration data 260, and the temperature data 262 to the data sets 314, 316, 318 and determines that the user is likely running from point C to point D. The controller 196 determines that activity data in FIG. 9 tends to show that the user is running more so than swimming or cycling from point C to point D. Thus, the controller 196 assigns activity type data 292 of "running" from point C to point D (step 664) to the verified data (step 656). Again the user data is updated (step 666) and it is determined whether additional data should be evaluated.

In this instance, further data from point D to point E remains for evaluation. Hence, the method 650 repeats at step 656 and the controller 196 evaluates the activity data from point D to point E. The activity data generated from point D to point E shows the effects of a user that has left the activity tracking device activated (i.e. generating activity data) after the completion of an activity, such as the exemplary triathlon of FIG. 9. That is, the desired athletic activities to be tracked ended at point D; however, the activity tracking device remained active until point E. The process used by the controller 196 to make this determination is described below.

The controller 196 processes the speed data 204 and determines an average speed 290 of about twenty-five miles per hour (25 mph). However, during the periods of twenty-five mile per hour average speeds, the user's motion data 218 has gone steady, the heart rate data 258 and respiration rate data 260 have both dropped to "at rest" values, and the temperature data 262 has fallen to normal values. Thus, using the data sets 314, 316, 318, the controller 196 determines that the speed data 204 and heart rate data 258 are not humanly capable (step 658) and do not correspond to any of the available activities (step 660). In particular, the average speed 290 is too high for the user to be running or swimming and the average heart rate 293 is too low for the user to be cycling at the average speed 290. Based on the above, the controller 196 determines that activity data in FIG. 9 tends to show that the user is not running, cycling, or swimming from point D to point E. Thus, the controller 196 generates activity type data 292 of "null" from point D to point E. The "Null" activity type corresponds to a stationary user, a user transitioning between activity types, or a user that is engaged in an activity type that is non-identifiable by the activity tracking system 100, such as a non-athletic pursuit. Accordingly, at step 662, an error message is displayed and the activity tracking is completed.

Overall, it is therefore determined that the user has likely participated in a triathlon that includes swimming, cycling and running. In this example, the user swam from point A to point B, cycled from point B to point C, ran from point C to point D, and then forgot to stop logging activity data and rides in an automobile over the duration of time represented from point D to point E.

As described in the foregoing paragraphs, it will be recognized that the controller 196 may use any combination of one or more of the different forms of activity data shown in FIG. 9 in order to determine the activity type data 292. While the activity type data 292 may be generated using only one of the forms of activity data shown in FIG. 9, it will be recognized that the use of additional forms of activity data provides additional information that may be useful in confirming the activity type being performed by the user. For example, the use of a combination of speed data 204, heart rate data 258, and motion data 218, will provide more reliable activity type data 292 than the use of speed data 204 alone.

The controller 196 may verify the activity data using any of various methods for verification of activity data, including those described above with reference to FIGS. 4-5 and FIGS. 7-8B. In particular, the controller 196 may assign a predetermined time period 297 to the activity data for each activity type, and then verify the activity data for each predetermined time period 297. Thereafter, the controller 196 evaluates the activity data in order to determine whether the activity data matches a predetermined data set or meets a given threshold.

With reference to the activity data from point A to point B in FIG. 9 that corresponds to the swimming activity type, the controller 197 assigns a predetermined time period 297 of one minute to the corresponding activity data. Moreover, the controller 197 uses a threshold average speed 294 of about five miles per hour (5.0 mph). Next, the controller 197 processes the average speed 290 of the speed data 204 to determine if the average speed of the user during any of the predetermined time periods 297 is greater than the threshold average speed 294. The average speed 290 for each predetermined time period 297 from point A to point B is less than the threshold average speed 294; thus, the controller 196 verifies the integrity of the activity data extending from point A to point B.

Considering the activity data from point B to point C in FIG. 9 that corresponds to the cycling activity type, the controller 197 assigns a predetermined time period 297 of two minutes to the corresponding activity data and a verified speed 294 of about forty miles per hour (40 mph). Next, the controller 197 processes the average speed 290 of the speed data 204 to determine if the average speed the user during any of the predetermined time period 297 is greater than the threshold average speed 294. The average speed 290 for each predetermined time period 297 from point B to point C is less than the threshold average speed 294; thus, the controller 196 verifies the integrity of the activity data extending from point B to point C.

Next, with reference to the activity data from point C to point D in FIG. 9 that corresponds to the running activity type, the controller 197 assigns a predetermined time period 297 of one minute to the corresponding activity data and a threshold average speed 294 of about eighteen miles per hour (18 mph). Next, the controller 197 processes the average speed of the speed data 204 to determine if the average speed 290 the user during any of the predetermined time periods 297 is greater than the threshold average speed 294. The average speed 290 for each predetermined time period 297 from point C to point D is less than the threshold average speed 294; thus, the controller 196 verifies the integrity of the activity data extending from point C to point D.

The controller 197 did not assign an activity type to the activity data extending from point D to point E. Accordingly, the activity data from point D to point E cannot and is not verified by the controller 196, because in effect, the controller 196 has determined that the activity data generated from point D to point E does not correspond to an athletic endeavor. Moreover, in at least one embodiment, the controller 196 cannot verify the activity data without knowing the activity type, because the threshold average speed 294 and the predetermined time period 297 are based on the activity type.

After verifying the activity data from points A to point D, the controller 196 sends the activity data from point A to point D to the memory 132 and the user data 278 and data sets 314, 316, 318 are updated accordingly, as noted in blocks 664 and 666 of FIG. 6B. Whereas, the activity data from point D to point E is discarded and does not contribute or in any way affect the user data 278 and the data sets 314, 316, 318, as noted in block 662 of FIG. 6B. Thus, the method 650 prevents the user from accidentally corrupting the activity data generated from point A to point D due to inadvertently leaving the activity tracking device active from point D to point E during a nonathletic endeavor. Only the portion of the activity data that could not be verified is discarded.

The activity tracking system 100 and the associated method described herein solves a number of technical problems in the art by determining whether activity data collected by the system is verified activity data that may actually be attributed to an associated activity type (e.g., an athletic activity performed by the user). The activity tracking system 100 corrects or updates the activity type data 292 that is associated with activity data in real time or during processing of the activity data subsequent to the activity being performed. For example, if a user inadvertently indicates that a running activity type will occur, but instead of running the user rides a bicycle, the activity tracking system 100 can automatically detect the cycling activity type and change the activity type data 292 so that verifiable activity data is generated.

The activity tracking system 100 prevents users participating in group fitness events from cheating. For example, a group fitness event may require the participants to run 100 miles in a month. If a user configures the activity tracking system 100 to generate data for a running activity type, but instead of running the user rides a bicycle or rides in an automobile, the activity tracking system 100 will automatically detect that the user is not running and will not apply the generated activity data to the user's total mileage for the group fitness event.

In the exemplary embodiment described above and illustrated in FIG. 1, both the personal electronic device 104 and the sensor assembly 106 include sensors that are carried by the user while the user performs an activity to be tracked. Thus, in some embodiments, the user may carry both the personal electronic device 104 and the sensor assembly 106 while tracking an activity. In other embodiments, the user may not carry both the personal electronic device 104 and the sensor assembly 106. For example, the user may carry only the personal electronic device 104, which includes the GPS receiver 180, the altimeter 184, and the accelerometer 188. In such an embodiment, the personal electronic device 104 generates all of the activity data. As another example, the user may carry only sensor assembly 106, which includes the heart rate sensor 234, the respiration sensor 240, and the temperature sensor 244. In this embodiment, the activity data is generated by the sensors 234, 240, 244 and is stored in the memory 250 during the activity. The activity data is transferred to the personal electronic device 104 and/or the remote computer 124 after the activity is completed (as signified by e.g., a button press or other interaction) for processing according to the method 600. In yet another embodiment, the user carries a device including only one sensor and a memory for recording the generated activity data from the one sensor. For example, a device (not shown) may include only the GPS receiver 180 and a memory, such as the memory 192. Other exemplary activity tracking systems 100 may include a device having only the accelerometer 188, only the heart rate sensor 234, only the respiration sensor 240, and/or only the temperature sensor 244.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

The above described system and method solves a technological problem common in industry practice related to analysis of collected activity data. Moreover, the above-described system and method improves the functioning of the computer device by verifying collected data against other data for that activity type, while also allowing the user to switch between activities while automatically determining the new activity type.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of operating an activity tracking system, comprising:

generating electronic activity data with an activity tracking device of the activity tracking system, the activity data including speed data generated by a speed sensor of the activity tracking device;
receiving a user selection of one of a plurality of activity types with an input unit of the activity tracking device, the user selection is a first activity type;
processing the activity data with a controller of the activity tracking system to determine average speed data based on the speed data and whether the average speed data exceed a predetermined average speed assigned to the first activity type, the controller operably connected to the speed sensor to receive the activity data and operably connected to the input unit to receive the user selection;
when the average speed data exceed the predetermined average speed (i) preventing association of the first activity type with the activity data using the controller, and (ii) displaying an error message on a display of the activity tracking device to inform a user that a second activity type was performed in generating the activity data that is different than the first activity type,
wherein the first activity type includes running, walking, jogging, or hiking,
wherein the second activity type includes only activities which a human is not capable of performing without aid of a machine including riding a bicycle and riding in an automobile, and
wherein the predetermined average speed is an average speed that the user of the activity tracking system is incapable of achieving while performing the first activity type.

2. The method of claim 1, wherein:
the activity data further include heart rate data generated by a heart rate sensor of the activity tracking device, the heart rate sensor operably connected to the controller,
processing the activity data with the controller further includes determining average heart rate data based on the heart rate data, and determining whether the average heart rate data exceed a predetermined average heart rate assigned to the first activity type, and
the controller is configured to prevent association of the first activity type with the activity data, and to display the error message on the display only when (i) the average speed data exceed the predetermined average speed, and (ii) the average heart rate data are less than the predetermined average heart rate.

3. The method of claim 2, further comprising:
when the average speed data are less than or equal to the predetermined average speed and the average heart rate data are greater than or equal to the predetermined average heart rate (i) associating the first activity type with the activity data using the controller, and (ii) storing the activity data and the first activity type in a memory of the activity tracking device.

4. The method of claim 1, wherein:
the activity data further include (i) heart rate data generated by a heart rate sensor of the activity tracking device, the heart rate sensor operably connected to the controller, and (ii) temperature data generated by a temperature sensor of the activity tracking device, the temperature sensor operably connected to the controller,
processing the activity data with the controller further includes determining average heart rate data based on the heart rate data, determining whether the average heart rate data exceed a predetermined average heart rate assigned to the first activity type, and determining whether the temperature data are less than a predetermined body temperature, and
the controller is configured to prevent association of the first activity type with the activity data, and to display the error message on the display only when (i) the average speed data exceed the predetermined average speed, (ii) the average heart rate data are less than the predetermined average heart rate, and (iii) the temperature data are less than the predetermined body temperature.

5. The method of claim 4, further comprising:
when the average speed data are less than or equal to the predetermined average speed, the average heart rate data are greater than or equal to the predetermined average heart rate, and the temperature data are greater than or equal to the predetermined body temperature (i) associating the first activity type with the activity data with using the controller, and (ii) storing the activity data and the first activity type in a memory of the activity tracking device.

6. The method of claim 1, wherein the activity data are second activity data, the method further comprising:
generating electronic first activity data with the activity tracking device, the first activity data generated prior to the second activity data;
storing an individualized data set based on the first activity data in a memory, the memory included in a data server operably connected to the activity tracking device;
receiving the individualized data set with a transceiver of the activity tracking device; and
determining the predetermined average speed based on the individualized data set.

7. The method of claim 1, further comprising:
storing a generalized data set including activity data from a plurality of users in a memory, the memory included in a data server operably connected to the activity tracking device;
receiving the generalized data set with a transceiver of the activity tracking device; and
determining the predetermined average speed based on the generalized data set.

8. The method of claim 1, further comprising:
discarding the activity data when the average speed data exceed the predetermined average speed.

9. The method of claim 8, further comprising:
storing the activity data and data corresponding to the first activity type in an electronic data profile when the average speed data are less than the predetermined average speed.

10. The method of claim 1, wherein:
the first activity type further includes swimming,
the activity data further include altitude data generated by an altitude sensor of the activity tracking device, the altitude sensor operably connected to the controller,
processing the activity data with the controller further includes determining an instantaneous slope of the altitude data, and determining whether the instantaneous slope exceeds a predetermined threshold instantaneous slope value assigned to the first activity type, and
the controller is configured to prevent association of the first activity type with the activity data, and to display the error message on the display only when (i) the average speed data exceed the predetermined average speed, and (ii) the instantaneous slope exceeds the predetermined threshold instantaneous slope value.

11. An activity tracking system, comprising:
- a speed sensor configured to generate electronic activity data including speed data;
- a user input configured to receive a user selection of one of a plurality of activity types, the user selection is a first activity type;
- a display screen;
- a memory; and
- a controller operably connected to the speed sensor, the user input, the display screen, and the memory, the controller configured to process the activity data to determine average speed data based on the speed data and to determine whether the average speed data exceed a predetermined average speed assigned to the first activity type,
- wherein when the average speed data exceed the predetermined average speed the controller is further configured to (i) prevent association of the first activity type with the activity data using the controller, and (ii) display an error message on the display screen of the activity tracking system to inform a user that a second activity type was performed in generating the activity data that is different than the first activity type,
- wherein the first activity type includes running, walking, jogging, or hiking,
- wherein the second activity type includes only activities which a human is not capable of performing without aid of a machine including riding a bicycle and riding in an automobile, and
- wherein the predetermined average speed is an average speed that the user of the activity tracking system is incapable of achieving while performing the first activity type.

12. The activity tracking system of claim 11, wherein:
- the activity data further include heart rate data generated by a heart rate sensor of the activity tracking system, the heart rate sensor operably connected to the controller,
- the controller is further configured to process the activity data to determine average heart rate data based on the heart rate data, and to determine whether the average heart rate data exceed a predetermined average heart rate assigned to the first activity type, and
- the controller is configured to prevent association of the first activity type with the activity data, and to display the error message on the display screen only when (i) the average speed data exceed the predetermined average speed, and (ii) the average heart rate data are less than the predetermined average heart rate.

13. The activity tracking system of claim 12, wherein when the average speed data are less than or equal to the predetermined average speed and the average heart rate data are greater than or equal to the predetermined average heart rate, the controller is configured to (i) associate the first activity type with the activity data, and (ii) store the activity data and the first activity type in the memory of the activity tracking system.

14. The activity tracking system of claim 11, further comprising:
- a heart rate sensor configured to generate heart rate data, the heart rate sensor operably connected to the controller; and
- a temperature sensor configured to generate temperature data, the temperature sensor operably connected to the controller,
- wherein the controller is further configured to process the activity data to determine average heart rate data based on the heart rate data, determine whether the average heart rate data exceed a predetermined average heart rate assigned to the first activity type, and determine whether the temperature data are less than a predetermined body temperature, and
- wherein the controller is configured to prevent association of the first activity type with the activity data, and to display the error message on the display screen only when (i) the average speed data exceed the predetermined average speed, (ii) the average heart rate data are less than the predetermined average heart rate, and (iii) the temperature data are less than the predetermined body temperature.

15. The activity tracking system of claim 14, wherein when the average speed data are less than or equal to the predetermined average speed, the average heart rate data are greater than or equal to the predetermined average heart rate, and the temperature data are greater than or equal to the predetermined body temperature, the controller is further configured to (i) associate the first activity type with the activity data using the controller, and (ii) store the activity data and the first activity type in the memory of the activity tracking system.

16. The activity tracking system of claim 11, wherein the activity data are second activity data, and the controller is further configured to:
- generate electronic first activity data with the speed sensor, the first activity data generated prior to the second activity data;
- store an individualized data set based on the first activity data in another memory, the other memory included in a data server operably connected to the activity tracking system;
- receive the individualized data set with a transceiver of the activity tracking system; and
- determine the predetermined average speed based on the individualized data set.

17. The activity tracking system of claim 11, wherein the controller is further configured to:
- store a generalized data set including activity data from a plurality of users in another memory, the other memory included in a data server operably connected to the activity tracking system;
- receive the generalized data set with a transceiver of the activity tracking system; and
- determine the predetermined average speed based on the generalized data set.

18. The activity tracking system of claim 11, wherein the controller is further configured to discard the activity data when the average speed data exceed the predetermined average speed.

19. The activity tracking system of claim 18, wherein the controller is further configured to store the activity data and data corresponding to the first activity type in an electronic data profile when the average speed data are less than the predetermined average speed.

20. The activity tracking system of claim 11, further comprising:
- an altitude sensor configured to generate altitude data, the altitude sensor operably connected to the controller,
- wherein the first activity type further includes swimming,
- wherein the controller is further configured to process the activity data to determine an instantaneous slope of the altitude data, and to determine whether the instantaneous slope exceeds a predetermined threshold instantaneous slope value assigned to the first activity type, and wherein the controller is configured to prevent association of the first activity type with the activity data, and to display the error message on the display screen only when (i) the average speed data exceed the predetermined average speed, and (ii) the instantaneous slope exceeds the predetermined threshold instantaneous slope value.

21. A non-transient computer readable medium containing computer executable instructions which are configured to, when executed by a processor:

receive electronic activity data including speed data generated by a speed sensor of an activity tracking device;

receive a user selection of one of a plurality of activity types via an input unit of the activity tracking device, the user selection is a first activity type;

determine average speed data based on the speed data and whether the average speed data exceed a predetermined average speed assigned to the first activity type with a controller, the controller operably connected to the speed sensor to receive the activity data and operably connected to the input unit to receive the user selection; and when the average speed data exceed the predetermined average speed (i) prevent association of the first activity type with the activity data with using the controller, and (ii) display an error message on a display of the activity tracking device to inform a user that a second activity type was performed in generating the activity data that is different than the first activity type, wherein the first activity type includes running, walking, jogging, or hiking, wherein the second activity type includes only activities which a human is not capable of performing without aid of a machine including riding a bicycle and riding in an automobile, and wherein the predetermined average speed is an average speed that a user of the activity tracking system device is incapable of achieving while performing the first activity type.

* * * * *